United States Patent
Fraser et al.

(10) Patent No.: US 11,492,657 B2
(45) Date of Patent: Nov. 8, 2022

(54) METHOD TO GENERATE BIOCOMPATIBLE DENDRITIC POLYMERS FOR ANALYTE DETECTION WITH MULTIMODAL LABELING AND SIGNAL AMPLIFICATION

(71) Applicant: University of Southern California, Los Angeles, CA (US)

(72) Inventors: Scott E. Fraser, Glendale, AZ (US); Simon Restrepo, Culver City, CA (US); Joseph P. Dunham, Glendale, AZ (US)

(73) Assignee: University of Southern California

( * ) Notice: Subject to any disclaimer, the term of this patent is extended or adjusted under 35 U.S.C. 154(b) by 312 days.

(21) Appl. No.: 16/606,038

(22) PCT Filed: Feb. 28, 2018

(86) PCT No.: PCT/US2018/020308
§ 371 (c)(1),
(2) Date: Oct. 17, 2019

(87) PCT Pub. No.: WO2018/194755
PCT Pub. Date: Oct. 25, 2018

(65) Prior Publication Data
US 2020/0140921 A1    May 7, 2020

Related U.S. Application Data

(60) Provisional application No. 62/486,364, filed on Apr. 17, 2017.

(51) Int. Cl.
| | |
|---|---|
| *C12Q 1/682* | (2018.01) |
| *C12Q 1/6834* | (2018.01) |
| *C12Q 1/6841* | (2018.01) |
| *C12N 15/11* | (2006.01) |
| *G01N 21/64* | (2006.01) |

(52) U.S. Cl.
CPC .............. *C12Q 1/682* (2013.01); *C12N 15/11* (2013.01); *C12Q 1/6834* (2013.01); *C12Q 1/6841* (2013.01); *G01N 21/6428* (2013.01); *C12N 2310/531* (2013.01); *G01N 2021/6439* (2013.01)

(58) Field of Classification Search
CPC .... C12Q 1/682; C12Q 1/6834; C12Q 1/6841; C12N 15/11; C12N 2310/531; G01N 21/6428; G01N 2021/6439
See application file for complete search history.

(56) References Cited

U.S. PATENT DOCUMENTS

| | | |
|---|---|---|
| 7,632,641 B2 | 12/2009 | Dirks et al. |
| 7,727,721 B2 | 6/2010 | Pierce et al. |
| 8,105,778 B2 | 1/2012 | Dirks et al. |
| 8,124,751 B2 | 2/2012 | Pierce et al. |
| 2006/0228733 A1 | 10/2006 | Pierce et al. |
| 2016/0046934 A1 | 2/2016 | Han et al. |
| 2017/0189543 A1* | 7/2017 | Owen ............... A61K 38/28 |

FOREIGN PATENT DOCUMENTS

| | | |
|---|---|---|
| CA | 2408535 | 8/2009 |
| CN | 110799576 A | 2/2020 |
| EP | 1730161 B1 | 9/2010 |
| EP | 3612585 A1 | 2/2020 |
| JP | 2020516319 A | 6/2020 |
| WO | 2014028538 A2 | 2/2014 |
| WO | 2015184510 A1 | 12/2015 |
| WO | 2018/194755 A1 | 10/2018 |
| WO | 2020/132527 A1 | 6/2020 |

OTHER PUBLICATIONS

ISR and WO for PCT/US2018/020308 dated May 8, 2018, 16 pages.
Ma, C. et al., Rapid and enzyme-free nucleic acid detection based on exponential hairpin assembly in complex biological fluids, Analyst, 2016, 141:2883-2886.
Dirks, R.M. et al., Triggered amplification by hybridization chain reaction, PNAS, 2004, 101(43):15275-15278.
Yin, P. et al., Programming biomolecular self-assembly pathways, Nature Letters, 2008, 451:318-322.
EP 18787707.1 Extended European Search Report dated Nov. 27, 2020, 6 pages.
Bowling et al., Application of a novel and automated branchedDNA in situ hybridization method for the rapid and sensitive localization of mRNA molecules in plant tissues, Applications in Plant Sciences, 2014 vol. 2(4), pp. 1-5.
Choi et al., Programmable in situ amplification for multiplexed imaging of mRNA expression, Nat Biotechnol, 2010, vol. 28(11), pp. 1208-1212.
Choi et al., Next-generation in situ hybridization chain reaction:higher gain, lower cost, greater durability, ACS Nano. 2014, vol. 8(5), pp. 4284-4294.
Wang et al., A Novel in Situ RNA Analysis Platform for Formalin-Fixed,Paraffin-Embedded Tissues, The Journal of Molecular Diagnostics, 2012, vol. 14(1), pp. 22-29.

(Continued)

*Primary Examiner* — David C Thomas
(74) *Attorney, Agent, or Firm* — Nixon Peabody LLP; Linda B. Huber

(57) ABSTRACT

Described herein is a method to create dendritic biocompatible polymers from pairs of complementary dendritic nucleic acid monomers in a controlled manner, using polymerization triggers. The dendritic monomers are constituted of nucleic acids and an organic polymer capable of self-assembly. Each polymer contains approximately 200 dendrites that can be used to attach labels and constitute a biologically compatible signal amplification technology. Depending on the context this technology could be used to reveal the presence of a large variety of analytes such as specific nucleic acid molecules, small molecules, proteins, and peptides.

21 Claims, 20 Drawing Sheets

Specification includes a Sequence Listing.

(56) References Cited

OTHER PUBLICATIONS

International Search Report and Written Opinion for PCT/US2019/67987, dated Apr. 24, 2020, 12 pages.
Harroun et al., Programmable DNA Switches and their Applications, Nanoscale, 2018, vol. 10, Abstract Only.
Winkler et al., A Novel Concept for Ligand Attachment to Oligonucleotides via a 2'-Succinyl Linker, Nucleic Acids Research, 2004, vol. 32(2), pp. 710-718.
Notice of Reasons for Rejection for JP 2020-506292 dated Feb. 14, 2022, 6 pages.

* cited by examiner

Figure 1.
Fig. 1A
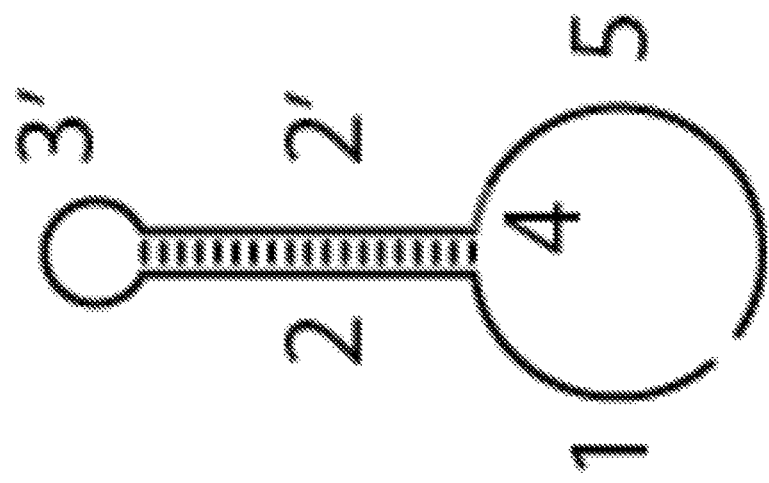
Fig. 1B
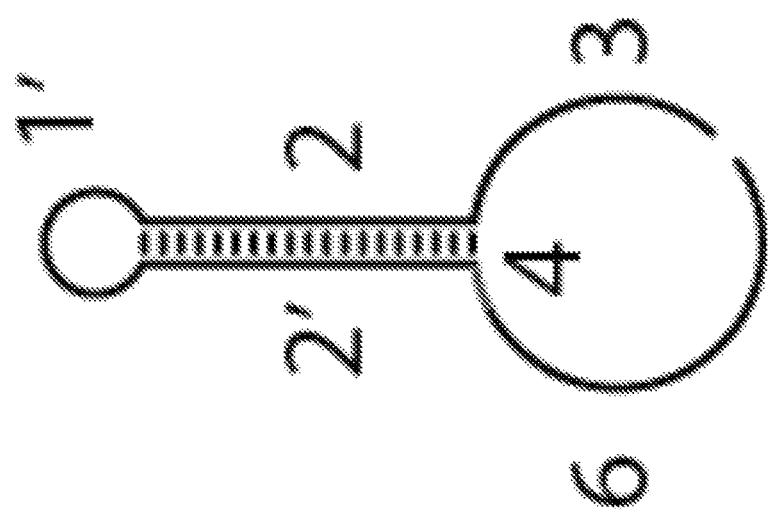
Fig. 1C
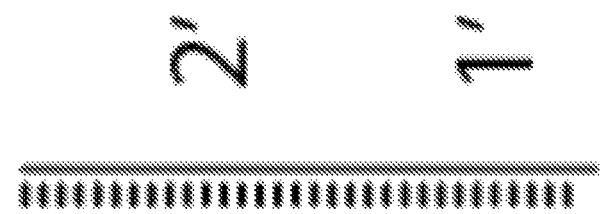

Figure 3.
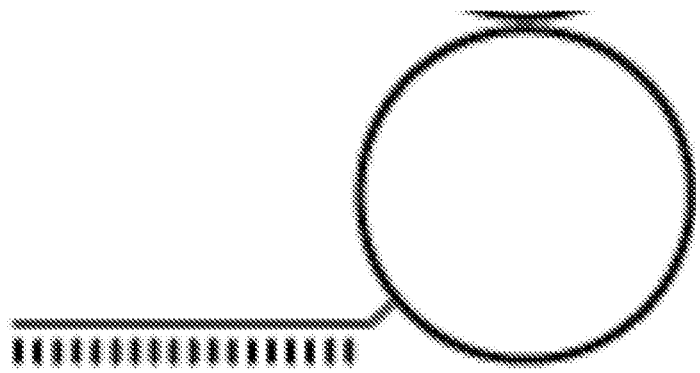
Fig. 3C
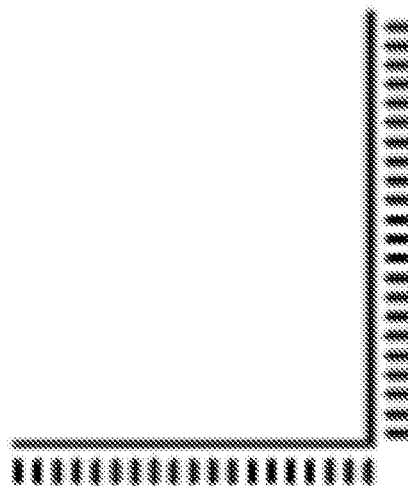
Fig. 3B
Fig. 3A

Figure 8.
Fig. 8A
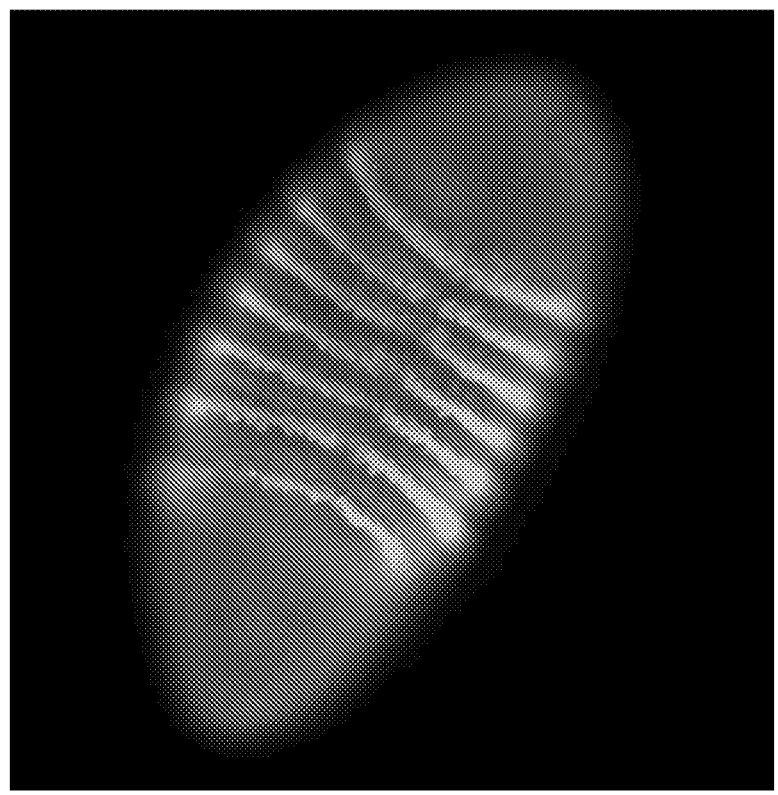
Fig. 8B
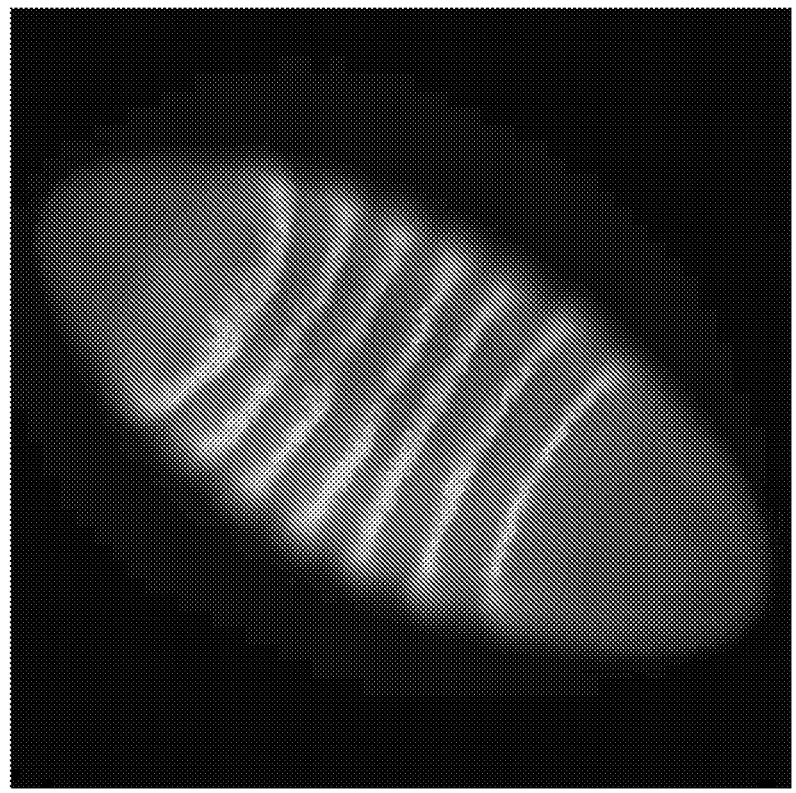

Figure 13.
Fig. 13B
Fig. 13A

METHOD TO GENERATE BIOCOMPATIBLE DENDRITIC POLYMERS FOR ANALYTE DETECTION WITH MULTIMODAL LABELING AND SIGNAL AMPLIFICATION

CROSS-REFERENCE TO RELATED APPLICATIONS

This application is a National Phase of International Application No. PCT/US2018/020308, filed Feb. 28, 2018, which designated the U.S. and that International Application was published under PCT Article 21(2) in English. This application claims priority under 35 U.S.C. § 119(e) to U.S. Provisional Application No. 62/486,364, filed Apr. 17, 2017, the contents of which are herein incorporated by reference in their entirety.

STATEMENT REGARDING FEDERALLY SPONSORED RESEARCH OR DEVELOPMENT

This invention was made with government support under HD075605 awarded by the National Institutes of Health. The government has certain rights in the invention.

FIELD OF THE INVENTION

Described herein are methods and compositions related to dendritic monomers for labeling and detecting analytes.

BACKGROUND

There is a need for innovative solutions to detect relevant analytes in complex mixtures. Most analytes do not have intrinsic signals to be used as detection labels. Hence, new technologies to label analytes with readily detectable markers such as chromogens or fluorophores are crucially needed. Further, technologies that enable signal amplification are generally preferable to direct labeling methods as they enhance the signal to noise ratio thereby increasing detection ease and accuracy. Furthermore, the best-suited label to employ can vary in a case specific basis that can depend on the nature of the sample, the analyte, or on the context of the analysis, for example. Thus, flexibility in the type of label that can be used and whose signal will be amplified constitutes another desired feature. An ideal analyte detection method would combine an easy way of detecting analytes, while providing label flexibility and signal amplification capacities. Thus, there is a great need in the art for labeling agents capable of binding to different biological moieties, while imparting signal amplification to generate high signal to noise ratios to benefit sensitivity, accuracy and reliability of detection.

Described herein is are methods and compositions that fulfill these criteria. Specifically, dendritic biocompatible polymers are generated from pairs of complementary dendritic nucleic acid monomers in a controlled manner, as initiated by the presence of polymerization triggers. The dendritic monomers are constituted of nucleic acids and an organic polymer. Each polymer contains approximately 200 dendrites that can be used to attach labels and constitute a biologically compatible signal amplification technology.

SUMMARY OF THE INVENTION

Described herein is an assembly, including at least two molecules, wherein each molecule includes a nucleic acid hairpin, a nucleic acid stem, a nucleic acid dendrite including a binding dendrite and extension dendrite, and an organic polymer, and further wherein the nucleic acid hairpin sequence of at least one first molecule is complementary to the nucleic acid binding dendrite sequence of at least one second molecule, and also wherein the nucleic acid hairpin sequence of the at least one second molecule is complementary to the nucleic acid binding dendrite sequence of the at least one first molecule and at least one nucleic acid trigger coupled to an analyte binding agent, wherein the nucleic acid trigger is complementary to the nucleic stem and the binding dendrite of at least first one molecule. In other embodiments, the hairpin sequence and binding dendrite sequence are about 10-24 nucleotides. In other embodiments, the hairpin sequence and binding dendrite sequence are about 6-10 nucleotides. In other embodiments, the hairpin sequence and binding dendrite sequence are about 11-13 nucleotides. In other embodiments, the extension dendrite includes about 10-20 nucleotides. In other embodiments, the extension dendrite includes about 13-16 nucleotides. In other embodiments, the extension dendrite includes about 10-25 nucleotides. In other embodiments, the nucleic acid trigger includes about 12-48 nucleotides. In other embodiments, the nucleic acid trigger includes about 34-38 nucleotides. In other embodiments, the nucleic acid stem includes about 12-30 nucleotides. In other embodiments, the nucleic acid stem includes about 6-15 nucleotides. In other embodiments, the nucleic acid stem includes about 22-26 nucleotides. In other embodiments, the organic polymer includes polyethylegene glycol. In other embodiments, the polyethylene glycol includes about 16-20 carbon lengths. In other embodiments, the analyte binding agent includes a polynucleotide. In other embodiments, the analyte binding agent includes a peptide or protein. In other embodiments, the analyte binding agent includes an antibody. In other embodiments, the method further includes a labeling polynucleotide complementary to an extension dendrite. In other embodiments, the labeling polynucleotide includes fluorophores, chromophores, chromogens, quantum dots, fluorescent microspheres, nanoparticles, elemental labels, metal chelating polymers, barcodes and/or sequential barcodes.

Further described herein is a method of polymerization, including adding at least two molecules, each including a nucleic acid and organic polymer, further adding a trigger molecule including a nucleic acid, and triggering self-assembled polymerization, wherein each molecule includes one or more complementary sequences to another molecule. In other embodiments, the at least two molecules each comprise a nucleic acid hairpin, a nucleic acid stem, a binding dendrite, an extension dendrite. In other embodiments, the nucleic acid trigger includes an analyte binding agent. In other embodiments, the method includes generating a detectable signal by binding a labeling polynucleotide complementary to another molecule, wherein the labeling polynucleotide includes a labeling agent. In other embodiments, the at least two molecules each comprise a nucleic acid hairpin, a nucleic acid stem, a nucleic acid dendrite including a binding dendrite and extension dendrite, and an organic polymer, and further wherein the nucleic acid hairpin sequence of at least one first molecule is complementary to the nucleic acid binding dendrite sequence of at least one second molecule, and also wherein the nucleic acid hairpin sequence of the at least one second molecule is complementary to the nucleic acid binding dendrite sequence of the at least one first molecule, and the at least one nucleic acid trigger is coupled to an analyte binding agent, wherein the nucleic acid trigger is complementary to the nucleic stem and the binding dendrite of at least first one molecule. In other embodiments, the method includes generating a detectable signal by binding a labeling polynucleotide to an extension dendrite, wherein the labeling polynucleotide includes a labeling agent.

BRIEF DESCRIPTION OF FIGURES

FIG. 1. System components. Two complementary dendritic monomers are shown each containing a tripartite structure of hairpin loop, stem, and nucleic acid dendrites, binding and extension dendrites, along with a organic polymer spacer (FIG. 1A & FIG. 1B). A nucleic acid trigger is shown (FIG. 1C). Nucleic acid domains binding dendrite 1-hairpin loop 1', stem 2-stem 2', and binding dendrite 3-hairpin loop 3' are complementary (i.e., 1-1', 2-2' and 3-3' are complementary and can hybridize). Domains 5-6 are the extension dendrites. Domain 4 (red) is a spacer element composed of an organic polymer that is crucial to maintaining monomer stability and facilitating dendrite function. The trigger (FIG. 1C) can bind to region 1 and open hairpin loop of the first molecule in FIG. 1A by branch migration (a similar hairpin of sequence 3'-2' could also be employed to open the second molecule of FIG. 1B). When hairpin A opens, this exposes the sequence 3'-2' which can act as a trigger for hairpin B which leads to the exposure of sequences 1'-2'. In this manner a dendritic polymer is formed by triggered self-assembly of monomeric units.

FIG. 3. Self-assembly mechanism. Nucleic acid triggers could be used directly (FIG. 3A), or attached to/extended by another nucleic acid oligonucleotide (FIG. 3B) or to a solid substrate such as a bead or a protein/peptide (FIG. 3C). Triggers can contain analyte binding agents, such binding agents can be specific for polynucleotides, peptide, proteins, antibodies, thereby allowing the amplification, polymerization process of FIGS. 1 and 2 to be a discrete, constituent step separate to the underlying "detection" technique wherein an analyte is bound to an analyte binding agent.

FIG. 8. In vivo labeling. FIG. 8A *Drosophila* embryo labeled with dendritic polymers (containing alexa-488 fluorophores as secondary labels) and revealing the expression domain of the segmentation gene even-skipped. FIG. 8B *Drosophila* embryo labeled with a fluorescent beacon generated by quadratic amplification (containing alexa-488 fluorophores) and revealing the expression domain of the segmentation gene even-skipped.

FIG. 13. Immunomuse. FIG. 13A GFP fusion protein as detected with an anti-GFP antibody conjugated to a MUSE trigger. FIG. 13B. *Drosophila* embryo labeled with dendritic polymers (containing alexa-488 fluorophores as secondary labels) and revealing an even-skipped exon.

Immunofluorescence assay employing an antibody against GFP and MUSE amplification with alexa-594fluorophores (shown in red).

Steric hindrance of hairpin stability.

Figure 16:
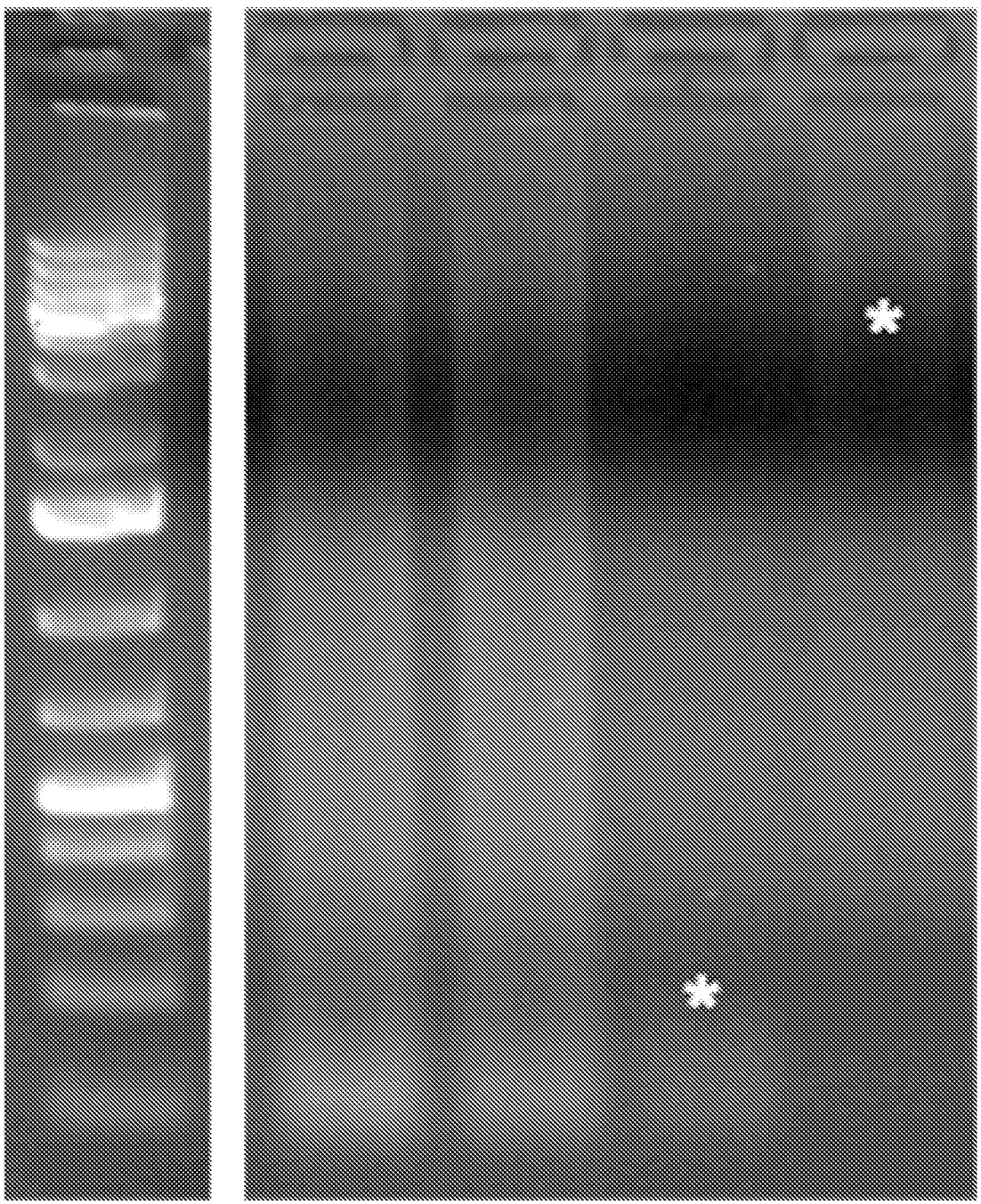

FIG. 16. Steric hindrance. MCP conjugated hairpins. (Lane 1) amplify in the absence of an initiator, whereas unconjugated hairpins remain stable (Lane 3). This indicates that the MCP strongly disturbs hairpin metastability. Further, whether in the absence (Lane 1) or presence of an initiator (Lane 2), amplification is ineffective as compared to unconjugated hairpins (Lane 4).

Figure 17:
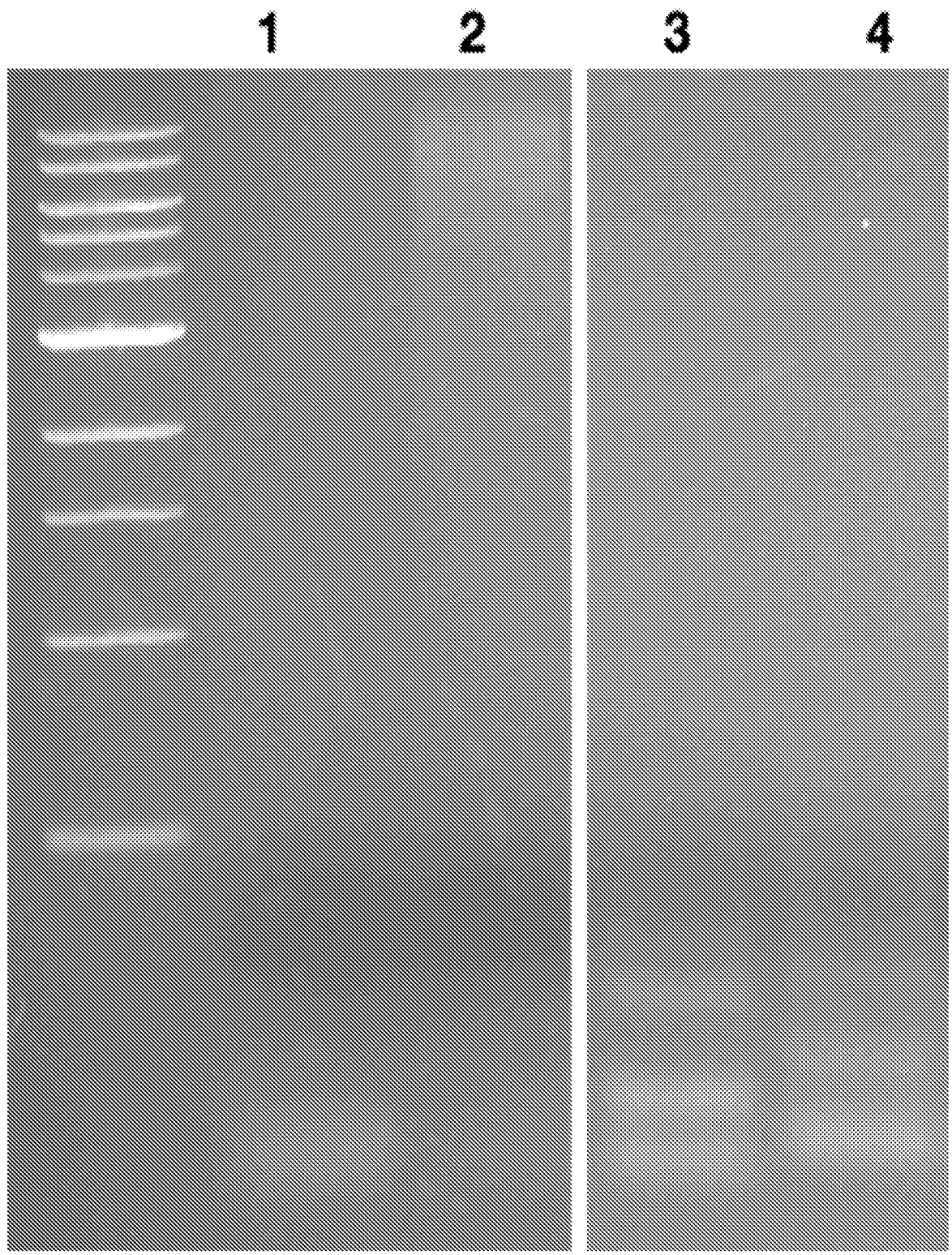

FIG. 17. Evidence for exceptional stability of very short MUSE hairpins. Very short MUSE hairpins (here 6 nt toehold, 10 nt stem, 16 nt dendrite) remain in their hairpin conformation in storage conditions such that, in the absence of snap-cooling, they do not amplify in the absence of an initiator (Lane 1) but amplify fully in presence of an initiator (Lane 2). In contrast, HCR hairpins are actually not hairpins in storage such that they amplify non-specifically (Lane 3) and poorly (Lane 4) when not snap-cooled into hairpin conformation just before the experiment is performed.

Figure 18:
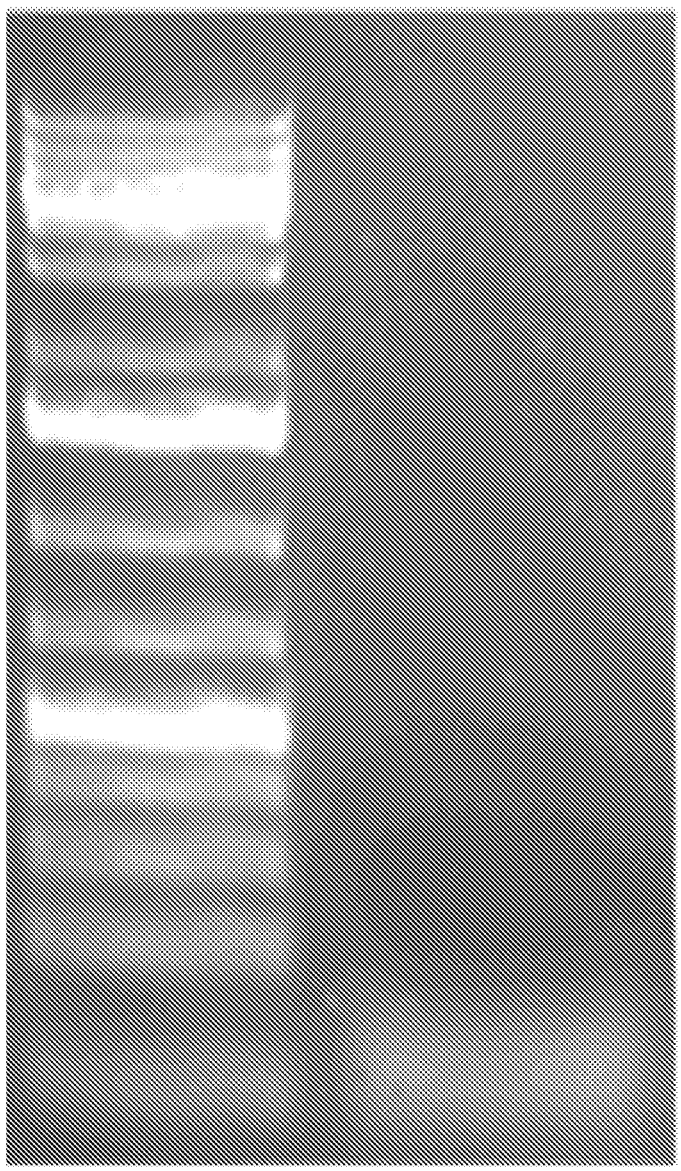
Figure 18:

FIG. 18. Rapid amplification of MUSE hairpins. Short MUSE hairpins ((here 10 nt toehold, 15 nt stem, 12 nt dendrite) amplify fully in 45 minutes (Lane 2) but do not amplify in the absence of an initiator (Lane 1).

Figure 19:
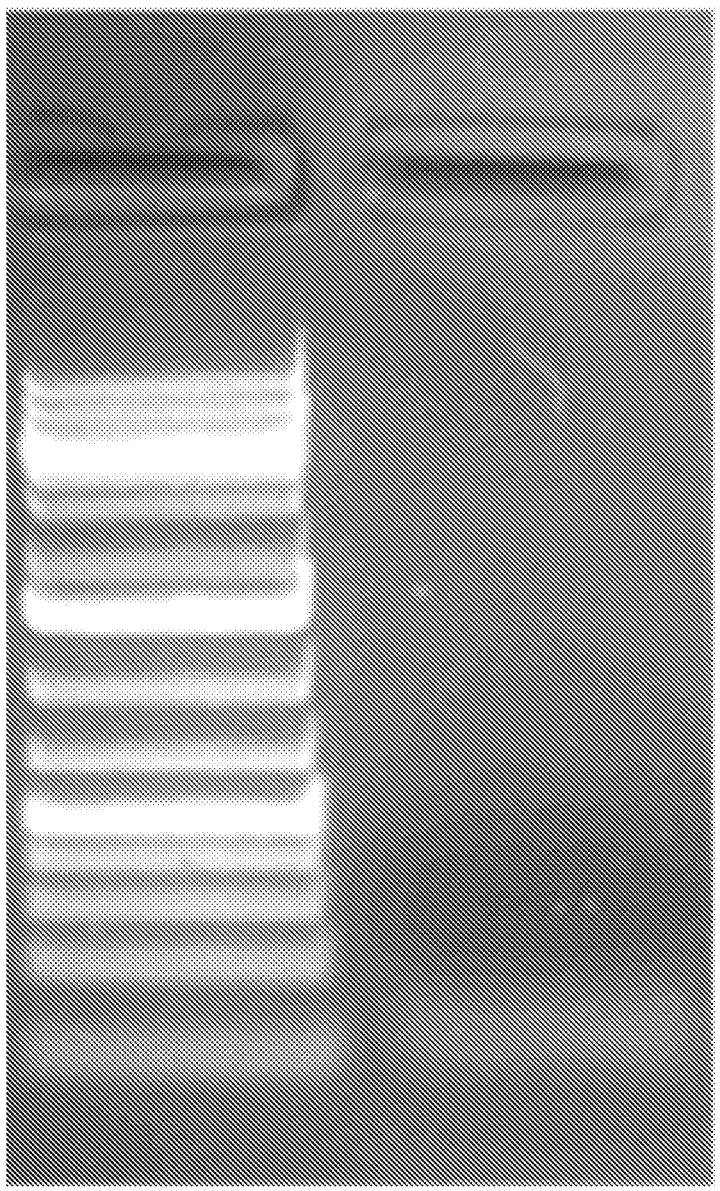
Figure 19:
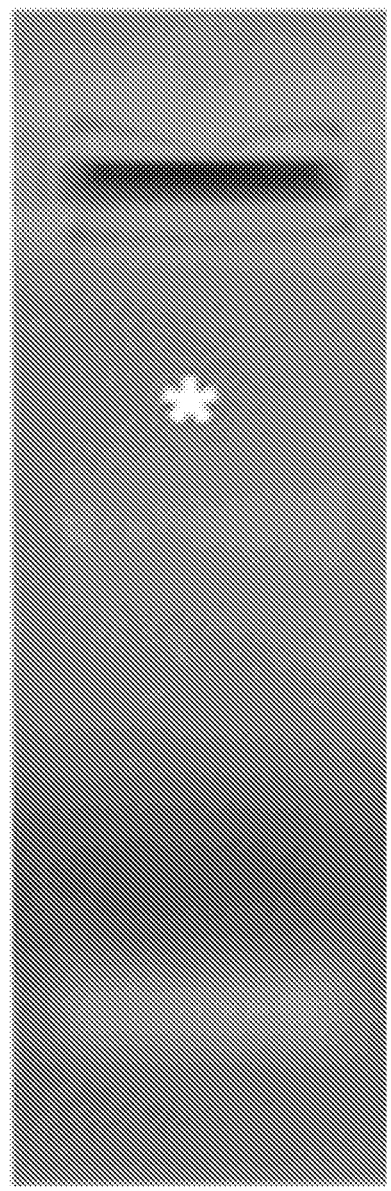

FIG. 19. Very rapid amplification of MUSE hairpins. Very short MUSE hairpins (here 6 nt toehold, 8 nt stem, 10 nt dendrite) amplify fully in 4 minutes (Lane 2) but do not amplify in the absence of an initiator (Lane 1).

As described, MUSE (Multimodal Universal Signal Enhancement) is a nanotechnology that enables signal amplification after the detection of analytes of interest. Compared to other detection and labeling techniques in the art, MUSE is highly versatile. First, MUSE can detect a variety of analytes and is almost completely agnostic to the detection scheme. Detection is performed as customary for the analyte in question (e.g., in situ hybridization for DNA and RNA analytes, immunohistochemistry for proteins and peptides). Second, MUSE is widely compatible with different labels like fluorophores, quantum dots and elemental labels. These two features allow for detection of virtually all types of biological macromolecules, who signal is output via any number of labels of choice. MUSE achieves this versatility by three constituent steps: detection, amplification and labeling. Traditional analyte detection schemes involve disadvantageous overlap of these constituent steps. For example, RNA in situ hybridization involves detection that is directly connected to labeling output, often in a linear fashion. PCR involves overlap between hybridization for detection, repeated hybridization confers amplification, amplification via repeated hybridization steps relates directly to output signal. By contrast, MUSE segregates constituent steps of detection, amplification, and labeling, by exploiting properties of self-assembling nucleic acid polymers. Amplification is achieved by the designed capability of monomers to self-assemble into dendritic polymers. As a result, output signal generation and propagation is segregated from amplification in a manner not achievable by traditional analyte detection schemes.

The described compositions and methods relying on dendritic polymers can be used to reveal the presence of a large variety of analytes including, specific nucleic acid molecules, small molecules, proteins, and peptides, thereby providing flexibility in detecting different biological moieties. The composition and methods includes i) a tri-partite molecule consisting of a nucleic acid hairpin loop, a stem, and nucleic acid dendrites further including an organic polymer "spacer" as shown in FIG. 1; ii) a polymerization trigger that includes a single stranded nucleic acid oligonucleotide; iii) an affinity ligand (i.e., analyte binding agent) used for analyte detection, whose composition can vary among nucleic acid oligonucleotides, protein, peptides, etc.

The tri-partite monomer is a key innovation of this technology that enables label flexibility while preserving monomer function. The generation of nucleic acid polymers from monomers has previously been achieved through Hybridization Chain Reaction (HCR). However, although branched monomers were envisioned as a means of achieving quadratic amplification (i.e., squared multiplier of n analyte molecules), existing monomers detection systems were only composed of nucleic acids. Nucleic acid hairpins are potentially destabilized or locked-in based on toehold-branch interactions. For this reason HCR approaches are strictly limited by the underlying nucleic acid chemistry to limit toehold-branch interactions.

To the Inventors' knowledge, successful quadratic amplification with nucleic acid branched hairpins has not been achieved. Additionally, no existing format utilizes both dendritic polymers for secondary label attachment and thus, cannot enable multimodal detection easily. In developing the described compositions and methods, the Inventors have also discovered that the rigidity of the nucleic acid backbone reduces the efficiency of secondary label hybridization, highlighting another limitation of nucleic acid branched polymers.

To correct for the limitations of branched nucleic acid polymers, an important innovation was development of an organic polymer "spacer" between the stem of the nucleic acid hairpin and the nucleic acid dendrite. The spacer minimizes interactions between the toehold and the dendrite, optimizes hairpin stability, minimizes steric hindrance during hybridization, changes the chemical properties of the monomer, and could be further functionalized (by choosing a photoclivable or hydrophilic spacer for example). Further, the spacer isolates the stem of the dendritic polymer from the dendrites by providing more flexibility and freedom of movement to the dendrite thus limiting steric hindrance and other potential interactions between the polymer stem and the labels. The design advantages of MUSE offer vastly superior approaches when compared to HCR.

Robust Tolerance of Variable Reagent Purity

For example, branched nucleic acid strategies like HCR typically require DNA oligos to be almost 100% pure, as truncated monomers can terminate the reaction. If 1/10 monomers are truncated, this would lead to aborted polymer growth after 10 units, on average. Only very meticulous denaturing PAGE electrophoresis permits level of purity nearing 100%. However, electrophoresis purification which molecules can be attached to the monomer oligos. Certain alexa fluorophores attachment chemistries (amino, thiol) are strongly affected by the reagents used during denaturing PAGE (urea, ammonium persulfate) such that it is not possible to have both 100% pure oligos and 100% conjugated (labeled) oligos. This is a disadvantage of existing branched nucleic acid technologies, and a direct consequence of when label attachment to oligos is not segregated from amplification steps.

MUSE provides a solution by separating amplification and labeling. The dendritic monomers can be readily purified by denaturing PAGE. The oligos that we use as labels can be ordered at about 80% purity via HPLC. In most cases, truncated labels are outcompeted by full length ones, thereby allowing for robust tolerance of variable purity for reagents. In addition, as MUSE labeled oligos are already of minimal length, truncated ones are likely not hybridize at all, thereby preventing premature termination of branching reactions. Thus, truncated label oligos do not affect signal amplification as dramatically as truncated monomers.

Reduction in Label Costs

Another advantage of MUSE is that it separates the costs of the monomers from the costs of the labels. Traditional branched nucleic acid technologies, like HCR, include monomers that are long and expensive. The necessity of PAGE purification further affects yield. A severe disadvantage of this approach is that effectuating the required attachment chemistry modifications and label molecules, is nevertheless lost due to the harsh purification steps required thereafter. Separating monomer and label synthesis also contributes to greater yield, which also reduces total costs.

The disadvantage of traditional branched DNA techniques is compounded when sets of labels or multiplexed labels are required for study. Traditional branched DNA techniques such as HCR, require a complete detection-amplification-label system for any alexa-fluor that want to employ. In contrast, MUSE controls costs by separating the costs of the attachment chemistry modification and labels from the costs of the hairpins. By keeping the amplification system constant, sets of labels or multiplexed labels can be achieved by label swapping. This is especially advantageous given the extra costs associated with the initiator presenting molecules. For MUSE, an initiator presenting molecules is associated one amplification system. With traditional branched DNA techniques, such as HCR, alteration of an alexa-fluor color (or eventually, the chemical nature of the label used), requires a full new detection-amplification-label system.

Advantages of the PEG Spacer

The polymeric PEG spacer further serves to separate amplification and labeling by breaking the continuity of the DNA phosphate backbone. This increases the flexibility at the dendrite-hairpin flexion point and minimizes the potential base-pairing interactions between the toehold and the dendrite. Instead of attempting to engineer dendritic hairpins consisting solely of DNA, which would be constrained by the nucleic acid design space available, one can alter the MUSE dendrite without modifying the hairpin sequences or vice-versa. This greatly simplifies the design of MUSE systems such that we could envisage having hundreds of systems operating in parallel. Further, it allows the optimization of the hairpin and dendrite sequences independently of one another such that one can design an optimal hairpin and an optimal dendrite. In the absence of a spacer this is not always possible.

Label Swapping

The possibility of swapping labels after amplification is an important advantage of MUSE compared to traditional branched DNA techniques. Sequential barcoding schemes such as seqFISH or MERFISH are becoming increasingly popular given that they enable the analysis of thousands of targets simultaneously. In seqFISH, HCR is employed to provide signal amplification. Each HCR polymer has to be digested with DNAses in between each barcoding round. Hence, each round takes approximately 24 hours.

By contrast, MUSE labels could be removed from the dendrites, for example with our label-erase-label approach, but also by lowering salt concentration in the buffer, or increasing temperature, or the use of reagents that lower the hybridization energy such as formamide. MUSE labels could be removed and swapped in approximately 2 hours per cycle. Since barcoding schemes require many rounds (up to 30) this results in significantly shorter procedures. Another instance of label swapping would involve multimodal label swapping instances. Here, a user could start an experiment with fluorescent labels to get high-resolution images of his sample and then quickly swap them with MCPs to obtain highly multiplexed data on the same sample.

Metastability

MUSE hairpins possess significant thermostability advantages over other branched DNA techniques, including HCR. HCR monomers are described as "metastable" (i.e., can maintain their hairpin configuration for a relatively long time, in solution at the concentration at which they are used). However, after some time, especially during storage and transportation they fall out of the hairpin secondary structure and adopt an even more stable and thermodynamically favorable homodimer configuration.

The Inventors discovered that short MUSE hairpins, including very short MSUE hairpins (toehold of 6-10 nucleotides, stem of less than 15 nucleotides) present different and superior chemical characteristics. These MUSE hairpins are beyond metastable as the only conformation they adopt is a hairpin structure. Some branched DNA techniques such as HCR require that hairpins be snap-cooled prior to an experiment to ensure formation. This is achieved by denaturing homodimers at 95° for 2-5 minutes and then cooled down to room temperature for 30 minutes. The latest MUSE hairpins can be employed directly from storage. Combined with the gains in amplification speed, described next, this change saves more than 18 hours from an HCR reaction. This is also important for the users as it makes MUSE a technique that can be employed in one work day.

Amplification Speed

HCR polymers need approximately 12 hours to reach their final size. Current MUSE systems need 1 hour to 15 minutes.

Described herein is an assembly including at least two molecules, each including a nucleic acid and organic polymer, a trigger molecule including a nucleic acid, wherein the at least two molecules and trigger molecule are configured for self-assembled polymerization, further wherein each molecule includes one or more complementary sequences to another molecule. In other embodiments, the at least two molecules each comprise a nucleic acid hairpin, a nucleic acid stem, a binding dendrite, an extension dendrite. In other embodiments, the nucleic acid trigger includes an analyte binding agent.

Further described herein is an assembly, including at least two molecules, wherein each molecule includes a nucleic acid hairpin, a nucleic acid stem, a nucleic acid dendrite includes a binding dendrite and extension dendrite, and an organic polymer, and further wherein the nucleic acid hairpin sequence of at least one first molecule is complementary to the nucleic acid binding dendrite sequence of at least one second molecule, and also wherein the nucleic acid hairpin sequence of the at least one second molecule is complementary to the nucleic acid binding dendrite sequence of the at least one first molecule and at least one nucleic acid trigger coupled to an analyte binding agent, wherein the nucleic acid trigger is complementary to the nucleic stem and the binding dendrite of at least first one molecule. In other embodiments, the hairpin sequence and binding dendrite sequence are about 6-10 nucleotides. In other embodiments, the hairpin sequence and binding dendrite sequence are about 10-24 nucleotides. For example, the hairpin sequence and binding dendrite includes 6, 7, 8, 9, or 10 nucleotides. In other embodiments, the hairpin sequence and binding dendrite sequence are about 11-13 nucleotides. In other embodiments, the extension dendrite includes 10-25, including 16-25 nucleotides. In other embodiments, the extension dendrite includes about 10-20 nucleotides. For example, the extension dendrite includes 16, 17, 18, 19, 20, 21, 22, 23, 24, or 25 nucleotides. In other embodiments, the extension dendrite includes about 13-16 nucleotides. In other embodiments, the nucleic acid trigger includes about 12-48 nucleotides. In other embodiments, the nucleic acid trigger includes about 34-38 nucleotides. In other embodiments, the stem is about 6-15 nucleotides. In other embodiments, the nucleic acid stem includes about 12-30 nucleotides. For example, the nucleic acid stem includes 6, 7, 8, 9 10, 11, 12, 13, 14, or 15 nucleotides. In other embodiments, the nucleic acid stem includes about 24 nucleotides. In other embodiments, the organic polymer includes polyethylegene glycol. Examples of assemblies of the above sequences configured for self-assembled polymerization include, at least two molecules, each including a binding dendrite and hairpin sequence of 6 nucleotides, a nucleic acid stem of 10 nucleotides, and an extension dendrite of 16 nucleotides, wherein each molecule includes one or more complementary sequences to another. Another example of assemblies of the above sequences configured for self-assembled polymerization include, at least two molecules, each including a binding dendrite and hairpin sequence of 8 nucleotides, a nucleic acid stem of 10 nucleotides, and an extension dendrite of 18 nucleotides, wherein each molecule includes one or more complementary sequences to another. A further example of assemblies of the above sequences configured for self-assembled polymerization include, at least two molecules, each including a binding dendrite and hairpin sequence of 10 nucleotides, a nucleic acid stem of 15 nucleotides, and an extension dendrite of 25 nucleotides, wherein each molecule includes one or more complementary sequences to another.

In other embodiments, the polyethylene glycol includes about 16-20 carbon lengths. In other embodiments, the polyethylene glycol includes about 2 nm in length. In other embodiments, the polyethylene glycol includes about 3-8 base pairs in length. In other embodiments, the polyethylene glycol includes about 4 base pairs in length. In various embodiments, the polymer connects the nucleic acid stem to a dendrite. In various embodiments, the at least two molecules are each monomers including a hairpin sequence of about 6-10 nucleotides, a nucleic acid stem of about 6-15 nucleotides, a binding dendrite of about 6-10 nucleotides, an extension dendrite of about 10-25, including 16-25 nucleotides, and a polymer of about 16-20 carbon lengths. In various embodiments, the at least two molecules are each monomers including a hairpin sequence of about 11-13 nucleotides, a nucleic acid stem of about 22-26 nucleotides, a binding dendrite of about 11-13 nucleotides, an extension dendrite of about 13-16 nucleotides, and a polymer of about 16-20 carbon lengths. In other embodiments, the analyte of interest includes nucleic acid. In other embodiments, the analyte of interest includes small molecules. In other embodiments, the analyte of interest includes polymers. In other embodiments, the analyte of interest includes peptides or proteins.

In other embodiments, the analyte binding agent includes a polynucleotide. In other embodiments, the analyte binding agent includes a peptide or protein. In other embodiments, the analyte binding agent includes an antibody. In other embodiments, the analyte binding agent includes peptides or proteins. In other embodiments, the analyte binding agent includes a peptide nucleic acid. In other embodiments, the analyte binding agent includes a locked nucleic acid.

In other embodiments, the assembly includes a labeling polynucleotide complementary to an extension dendrite. In other embodiments, the labeling polynucleotide includes fluorophores, chromophores, chromogens, quantum dots, fluorescent microspheres, nanoparticles, elemental labels, metal chelating polymers, barcodes and/or sequential barcodes, including any number of other labeling agents known to one of ordinary skill in the art.

In various embodiments, fluorophores include fluorescein, rhodamine, Alexa Fluors, DyLight fluors, ATTO Dyes, or any analogs or derivatives thereof. In some embodiments, labels of the present invention include but are not limited to fluorescein and chemical derivatives of fluorescein; Eosin; Carboxyfluorescein; Fluorescein isothiocyanate (FITC); Fluorescein amidite (FAM); Erythrosine; Rose Bengal; fluorescein secreted from the bacterium *Pseudomonas aeruginosa*; Methylene blue; Laser dyes; Rhodamine dyes (e.g., Rhodamine, Rhodamine 6G, Rhodamine B, Rhodamine 123, Auramine O, Sulforhodamine 101, Sulforhodamine B, and Texas Red).] In various embodiments, labels of the present invention include Alexa Fluor family of fluorescent dyes, including Alexa-350, Alexa-405, Alexa-430, Alexa-488, Alexa-500, Alexa-514, Alexa-532, Alexa-546, Alexa-555, Alexa-568, Alexa-594, Alexa-610, Alexa-633, Alexa-647, Alexa-660, Alexa-680, Alexa-700, or Alexa-750.

In various embodiments, quantum dots include semiconductor nanocrystal. In various embodiments, semiconductors are constructed of elements from groups II-VI, III-V and IV of the periodic table. In various embodiments, quantum dots include ZnS, ZnSe, ZnTe, CdS, CdSe, CdTe, GaN, GaP, GaAs, GaSb, InP, InAs, InSb, AlS, AlP, AlAs, AlSb, PbS, PbSe, Ge, and Si and ternary and quaternary mixtures thereof. In various embodiments, the quantum dots include an overcoating layer of a semiconductor having a greater band gap. In various embodiments, the semiconductor nanocrystals are characterized by their uniform nanometer size. By "nanometer" size, it is meant less than about 150 Angstroms (Å), and preferably in the range of 12-150 Å.

In various embodiments, the assembly further includes an additional at least two molecules, and a linker molecule including a nucleic acid sequence address complementary to one or more extension dendrites of the initial at least two molecules and a secondary trigger for the additional at least two molecules, wherein the additional at least two molecules and linker molecule are configured for self-assembled polymerization. In various embodiments, the initial at least two molecules and trigger are a first self-assembled polymerization, and the additional at least two molecules and a linker molecule are a second self-assembled polymerization. In various embodiments, the first and second self-assembled polymerization are a quadratic amplification. In other embodiments, the assembly includes a labeling polynucleotide complementary to an extension dendrite of the additional at least two molecules.

Further described herein is a kit of the assembly including at least two molecules, wherein each molecule includes a nucleic acid hairpin, a nucleic acid stem, a nucleic acid dendrite includes a binding dendrite and extension dendrite, and an organic polymer, and further wherein the nucleic acid hairpin sequence of at least one first molecule is complementary to the nucleic acid binding dendrite sequence of at least one second molecule, and also wherein the nucleic acid hairpin sequence of the at least one second molecule is complementary to the nucleic acid binding dendrite sequence of the at least one first molecule and at least one nucleic acid trigger coupled to an analyte binding agent, wherein the nucleic acid trigger is complementary to the nucleic stem and the binding dendrite of at least first one molecule, and instructions for use of the kit. In various embodiments, the at least two molecules, and trigger are configured for self-assembled polymerization. In various embodiments, the assembly is capable of generating a polymer including 25-50 units of first, second molecules and nucleic acid trigger sub-assemblies, about 50-100 units of first, second molecules and nucleic acid trigger sub-assemblies, about 100-150 units of first, second molecules and nucleic acid trigger sub-assemblies, about 150-200 units of first, second molecules and nucleic acid trigger sub-assemblies, or 200 or more units of first, second molecules and nucleic acid trigger sub-assemblies.

In various embodiments, the kit further includes introduction of an additional at least two molecules, and a linker molecule including a nucleic acid sequence address complementary to one or more extension dendrites of the initial at least two molecules and a secondary trigger for the additional at least two molecules, wherein the additional at least two molecules and linker molecule are configured for self-assembled polymerization. In various embodiments, the assembly is capable of generating a polymer including 25-50 units of additional first, second molecules and linker sub-assemblies, about 50-100 units of additional first, second molecules and linker sub-assemblies, about 100-150 units of additional first, second molecules and linker sub-assemblies, about 150-200 units of additional first, second molecules and linker trigger sub-assemblies, or 200 or more units of additional first, second molecules and linker trigger sub-assemblies.

In other embodiments, the kit includes a labeling polynucleotide complementary to an extension dendrite of the initial at least two molecules, and/or additional at least two molecules. In various embodiments, the kit includes two or more labeling polynucleotides, each of which is complementary to one or more extension dendrites of the initial at least two molecules and/or additional at least two molecules.

Described herein is a method of polymerization, including adding at least two molecules, each including a nucleic acid and organic polymer, further adding a trigger molecule includes a nucleic acid, and triggering self-assembled polymerization, wherein each molecule includes one or more complementary sequences to another molecule. In other embodiments, the at least two molecules each comprise a nucleic acid hairpin, a nucleic acid stem, a binding dendrite, an extension dendrite. In other embodiments, the nucleic acid trigger includes an analyte binding agent. In other embodiments, generating a detectable signal by binding a labeling polynucleotide complementary to another molecule, wherein the labeling polynucleotide includes a labeling agent. In other embodiments, the at least two molecules each comprise a nucleic acid hairpin, a nucleic acid stem, a nucleic acid dendrite includes a binding dendrite and extension dendrite, and an organic polymer, and further wherein the nucleic acid hairpin sequence of at least one first molecule is complementary to the nucleic acid binding dendrite sequence of at least one second molecule, and also wherein the nucleic acid hairpin sequence of the at least one second molecule is complementary to the nucleic acid binding dendrite sequence of the at least one first molecule, and the at least one nucleic acid trigger is coupled to an analyte binding agent, wherein the nucleic acid trigger is complementary to the nucleic stem and the binding dendrite of at least first one molecule. In other embodiments, generating a detectable signal includes binding a labeling polynucleotide to an extension dendrite, wherein the labeling polynucleotide includes a labeling agent. In other embodiments, the labeling agent includes fluorophores, chromophores, chromogens, quantum dots, fluorescent microspheres, nanoparticles, elemental labels, metal chelating polymers, barcodes and/or sequential barcodes, including any number of other labeling agents known to one of ordinary skill in the art. In various embodiments, the polymer connects the nucleic acid stem to a dendrite. In various embodiments, the at least two molecules are each monomers including a hairpin sequence of about 6-10 nucleotides, a nucleic acid stem of about 6-15 nucleotides, a binding dendrite of about 6-10 nucleotides, an extension dendrite of about 10-25, including 16-25 nucleotides, and a polymer of about 16-20 carbon lengths. In various embodiments, the at least two molecules are each monomers including a hairpin sequence of about 11-13 nucleotides, a nucleic acid stem of about 12-30 nucleotides, a binding dendrite of about 11-13 nucleotides, an extension dendrite of about 13-16 nucleotides, and a polymer of about 16-20 carbon lengths. In other embodiments, the nucleic acid trigger includes about 12-48 nucleotides. In various embodiments, the polymer connects the nucleic acid stem to a dendrite. In various embodiments, the at least two molecules are added in a ratio to nucleic acid trigger of about 1:25, 1:50, 1:100, 1:200 and all ranges in between.

Figure 2:
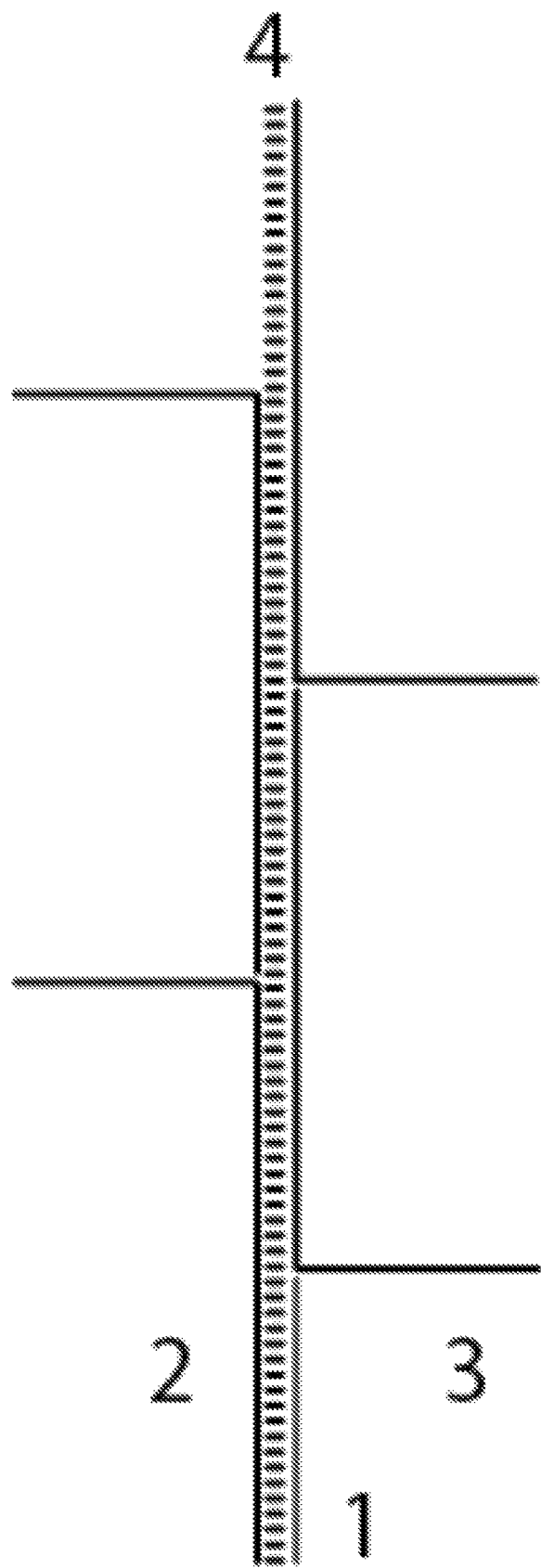
FIG. 2. Components when assembled. Dendritic polymer (4) created by the chemical interaction between the trigger (1), and complementary dendritic monomers (2). Note the extension dendrites extending from the polymer (3).

For example, as depicted in FIG. 1, the binding dendrimer 1 of the first molecule in FIG. 1A is complementary to hairpin 1' of the second molecule in FIG. 1B. The first and second molecules each contain a stem including complementary nucleic acid sequence 2-2'. A hairpin sequence 3 of the first molecule in FIG. 1A is complementary to the binding dendrite 3' of the second molecule in FIG. 1B. The first molecule in FIG. 1A includes an extension dendrite 5; the second molecule in 1B include another extension dendrite 6. Both first and molecules of FIGS. 1A and 1B, respectively, include a spacer domain 4 that can include an organic polymer. A third molecule, the nucleic acid trigger of FIG. 1C can bind to binding to binding dendrite 1 of the first molecule of FIG. 1A and open the first molecule (a similar hairpin of sequence 3'-2' could also be employed). Opening of the first molecule of FIG. 1A exposes the sequence hairpin 3' and stem 2', which operates as a trigger for the hairpin 3 and stem 2' of the second molecule of FIG. 1B. Exposure of the hairpin 1' and stem 2' of the second molecule operates similarly as the initial nucleic acid trigger, again opening of another first molecule, leading to opening of another second molecule. In this manner a dendritic polymer is formed by triggered self-assembly. A resulting polymer of the assembled first and second molecules, and trigger is shown in FIG. 2. The extension dendrite 5 and/or 6 can each, or both, directly bind to analyte, labels, or additional polymers.

Figure 6:
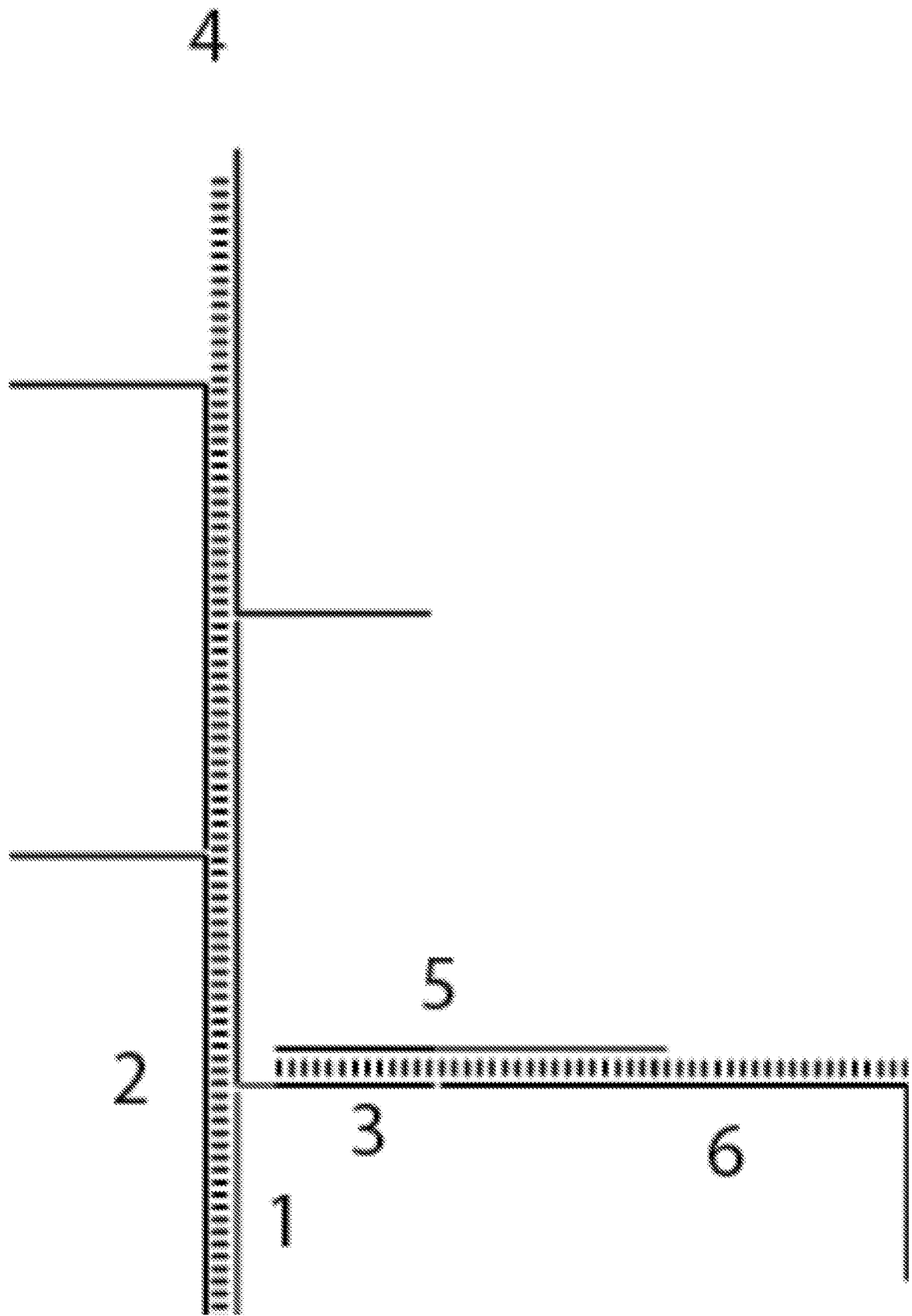
FIG. 6. Example of a quadratic amplification strategy. A linker oligo (5) containing an "address" and a secondary trigger sequence (blue in 5) is used to seed a second polymerization event and hence, an additional round of amplification. This results in a quadratic amplification (i.e., square multiplier of n analyte molecules).
Figure 7:
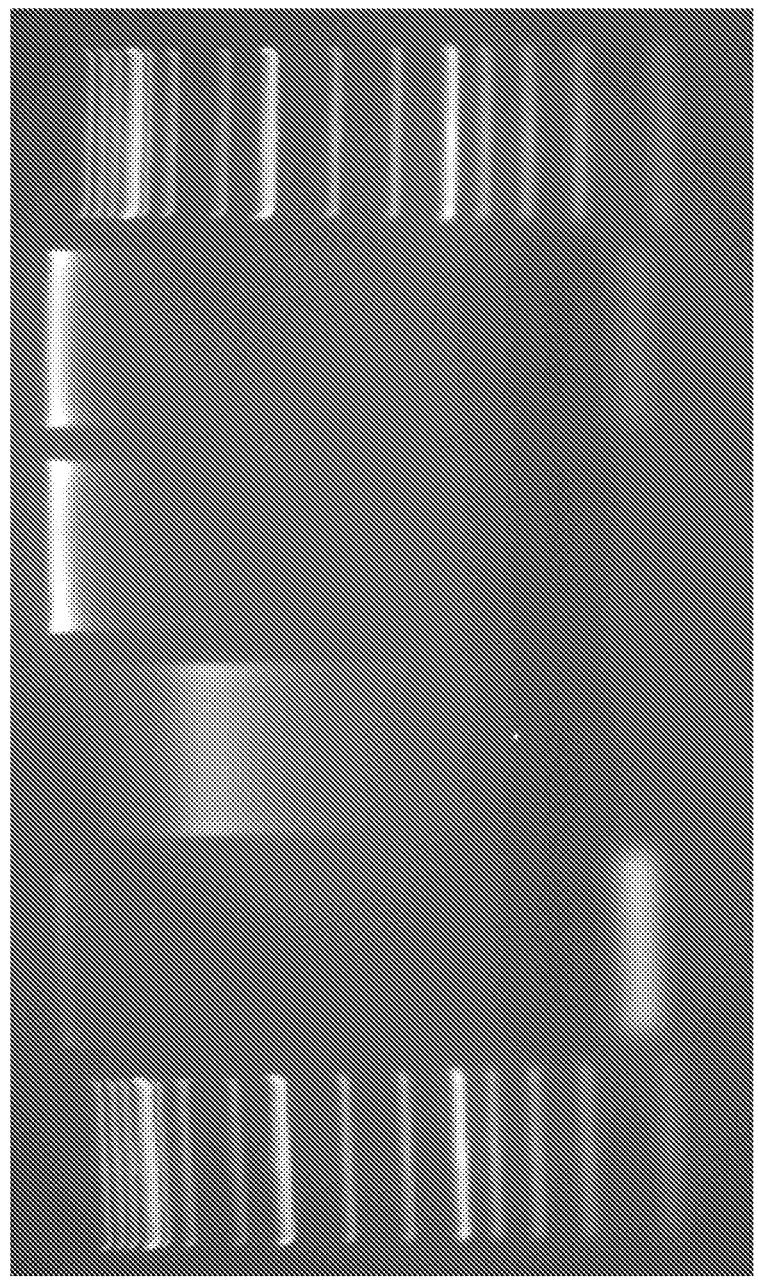
FIG. 7. Agarose gel electrophoresis. From left: dna ladder, monomers only, monomers to initiator (i.e. trigger) ratio 1/10, monomers to initiator ratio 1/50, monomers to initiator ratio 1/100, dna ladder. Note the presence of abundant high molecular weight molecules on lanes 4-5 at the top of the gel and the absence of monomers at the bottom (all monomers are now incorporated in the polymer). In contrast, on lane 2 (monomers only) only background signal amplification has occurred and most monomers are at the bottom of the gel.
Figure 9:
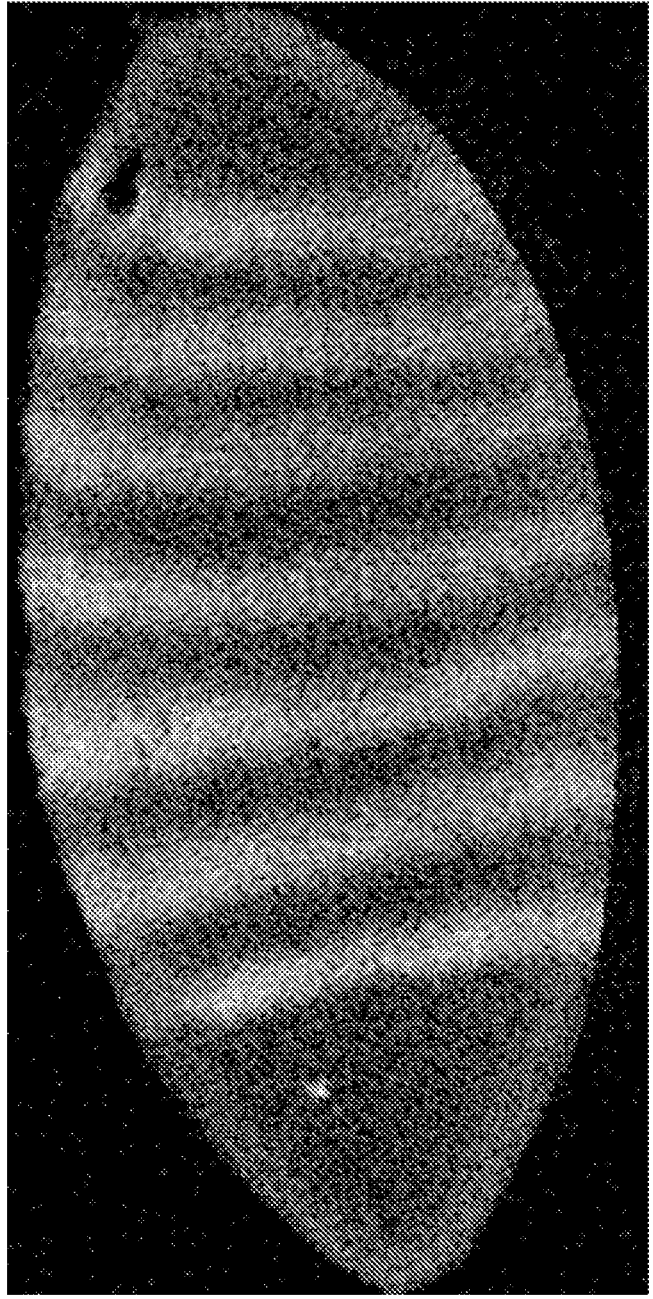
FIG. 9. In vivo labeling. *Drosophila* embryo labeled with dendritic polymers (with secondary labels containing Europium 151) and revealing the expression domain of the segmentation gene even-skipped.
Figure 10:
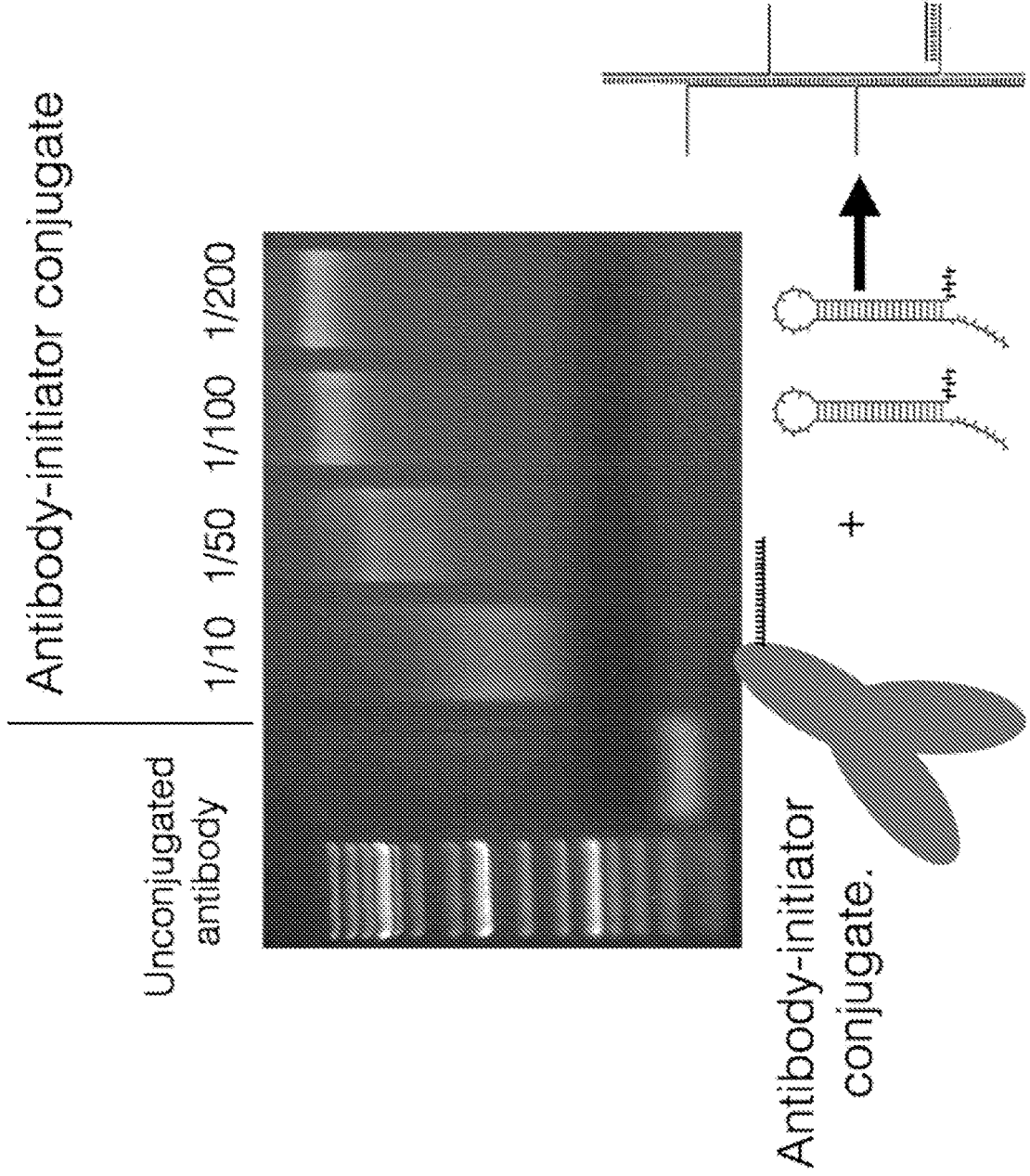
FIG. 10. Antibody based detection. In another embodiments, here it is demonstrated that one can generate dendritic polymers originating from antibodies conjugated to a polymerization trigger/initiator. The amplification is specific as no polymerization (high molecular weight bands) is seen on the unconjugated antibody lane but only the low molecular weight monomers.
Figures 11, 11A:
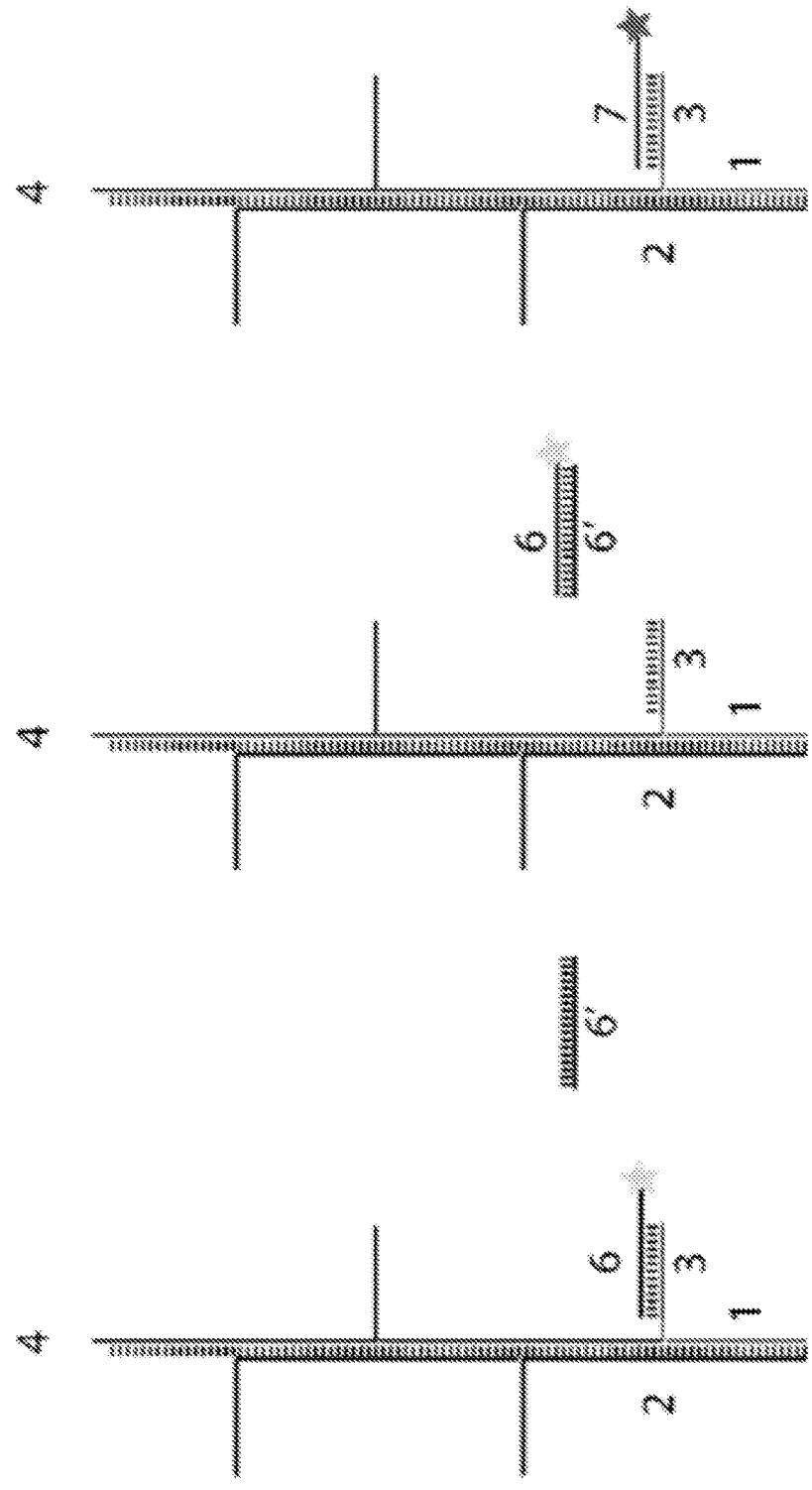
FIG. 11. Barcode detection schemes.
FIG. 11A. The label-erase-label approach works with by alternating labeling oligonucleotides (6) that are complementary to the MUSE dendrite (3) and contain an extra 6-10 nucleotide long overhang. An eraser oligonucleotide (6') that is fully complementary to the labeling oligonucleotide sequence can be used to remove the labeling oligonucleotide by branch migration. This enables the addition of a new labeling oligonucleotide with a different fluorophore (7).
Figures 11, 11B:
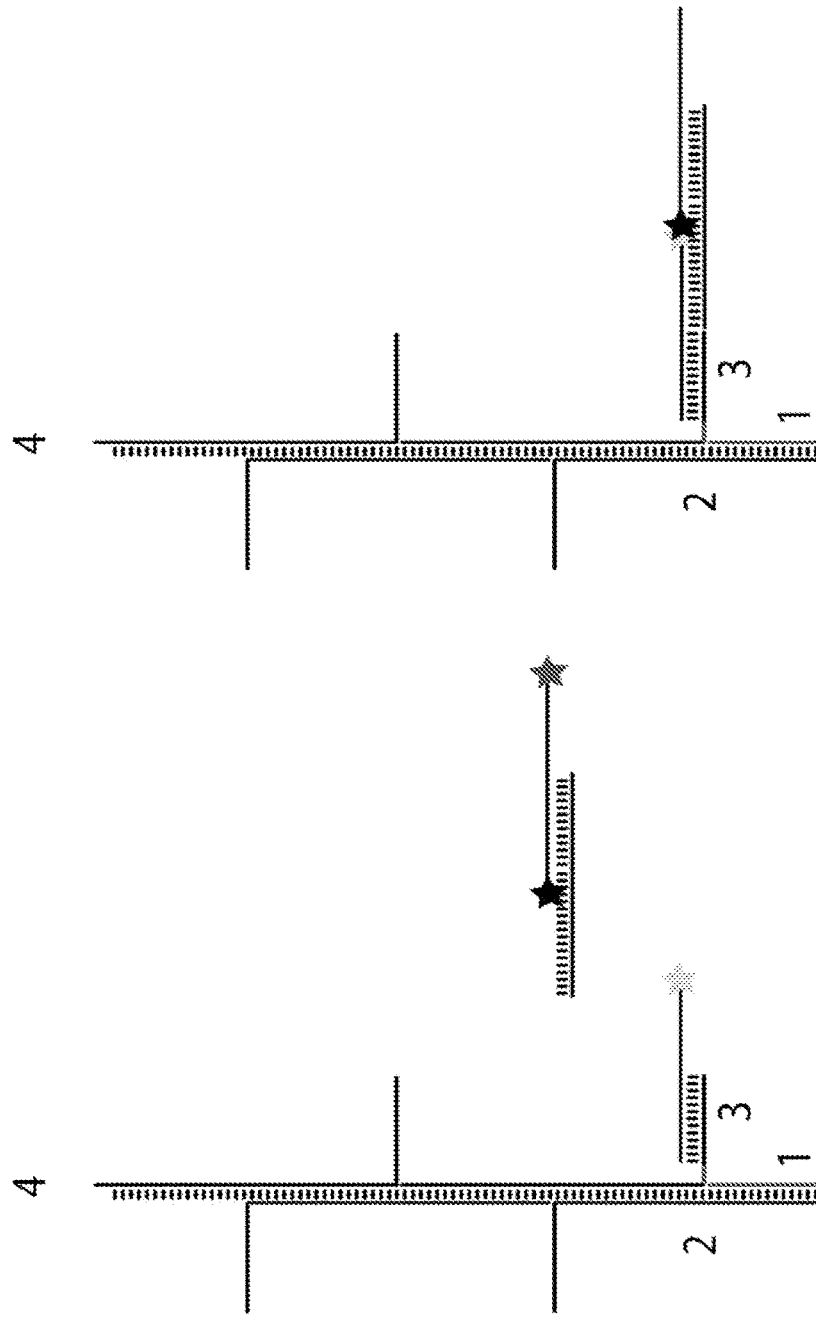
FIG. 11B. In the label-quench-label technique, a first oligonucleotide complementary to a dendrite sequence on the dendritic polymer to label that contains an additional 15 nucleotide "overhang" sequence, constitutes the first barcode label. The "overhang" serves to anchor a dsDNA "quencher" label containing two overhangs, one complementary to the overhang of the first label and a second that will serve to anchor the next label. The "quencher" label oligonucleotide contains a short-distance quencher such as dabcyl and a fluorophore. The hybridization of the quencher label to the overhang of the previous label places the quencher and the previous fluorophore in very clos distance such that the fluorescence of the first fluorophore is quenched and only the fluorophore contained on the "quencher" label can emit a signal. In this manner, subsequent "quencher" labels can be hybridized to one another n times to generate a barcode.
Figure 12:
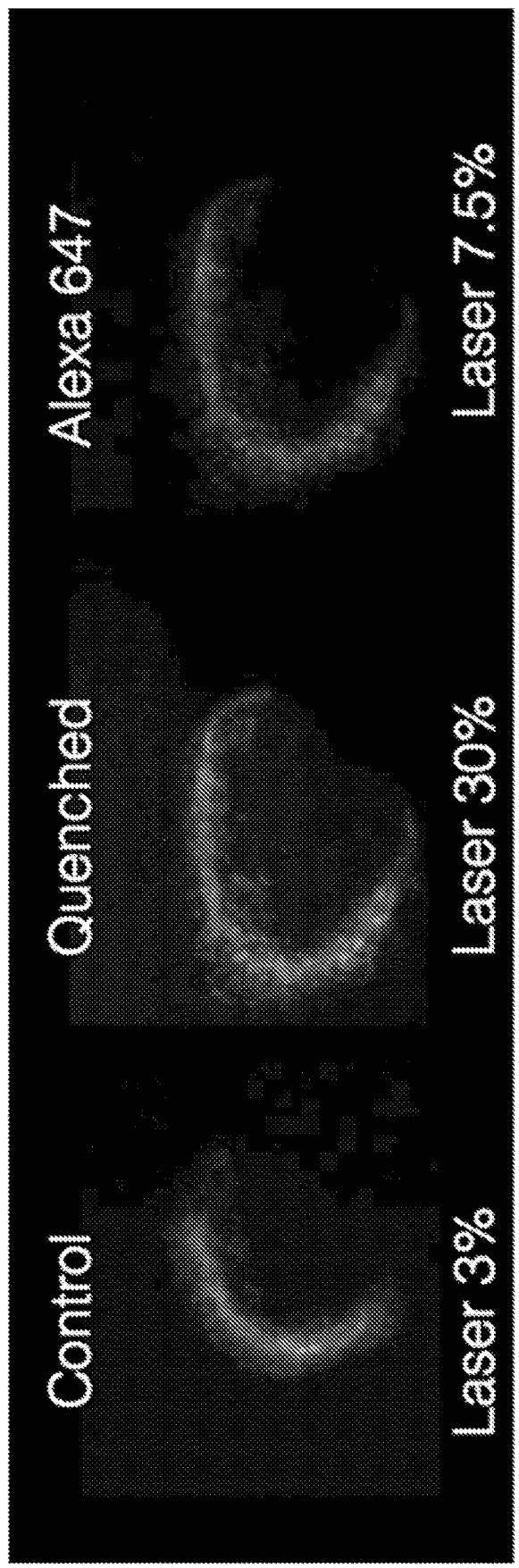
FIG. 12. Label-Quench-Label example. The control shows that 3% laser power is required to detect the transcript that is labeled with a dendritic polymer here, when no "quencher" label is present. The quenched result shows that the laser power had to be increased to 30% to detect the quenched signal. The Alexa 647 result confirms that in addition to the quencher, a second fluorophore was added to the structure.
Figure 14:
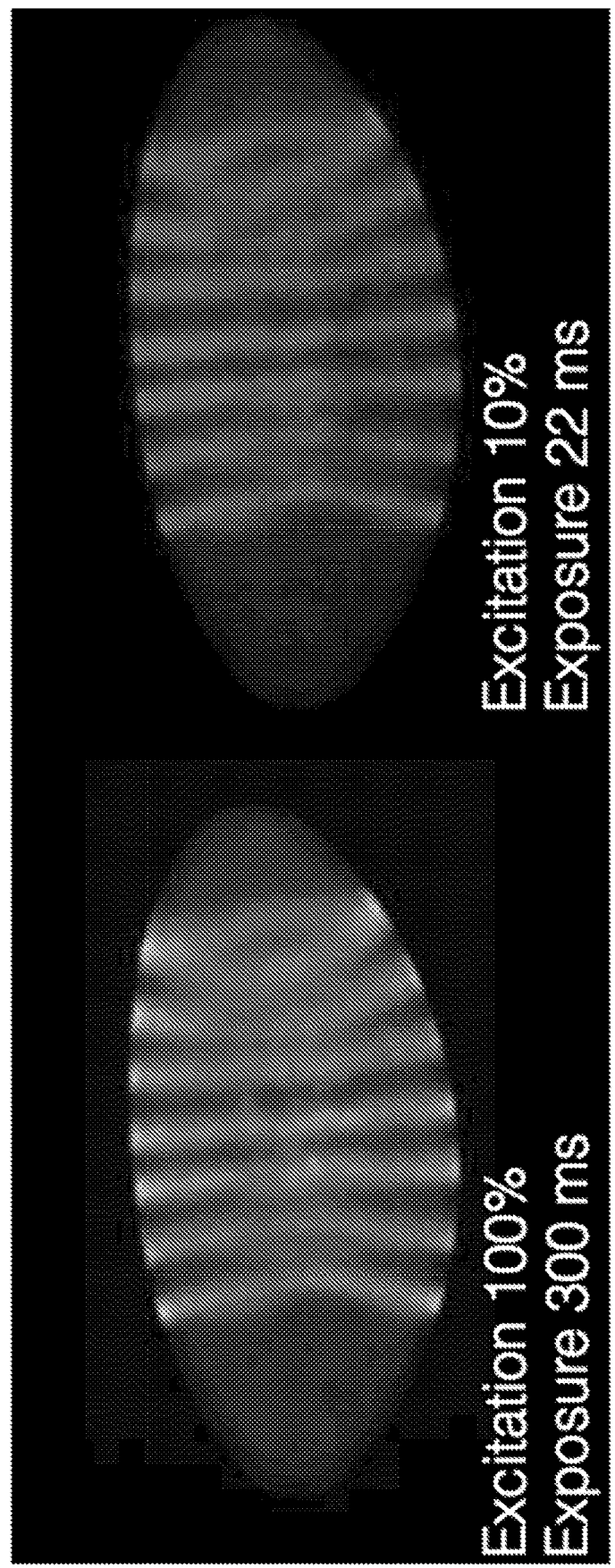
FIG. 14. Quantum dot labeling. *Drosophila* embryo labeled with dendritic polymers (containing QDot 655 labels) and revealing the expression domain of the segmentation gene even-skipped.
Figures 15, 15A, 15B:
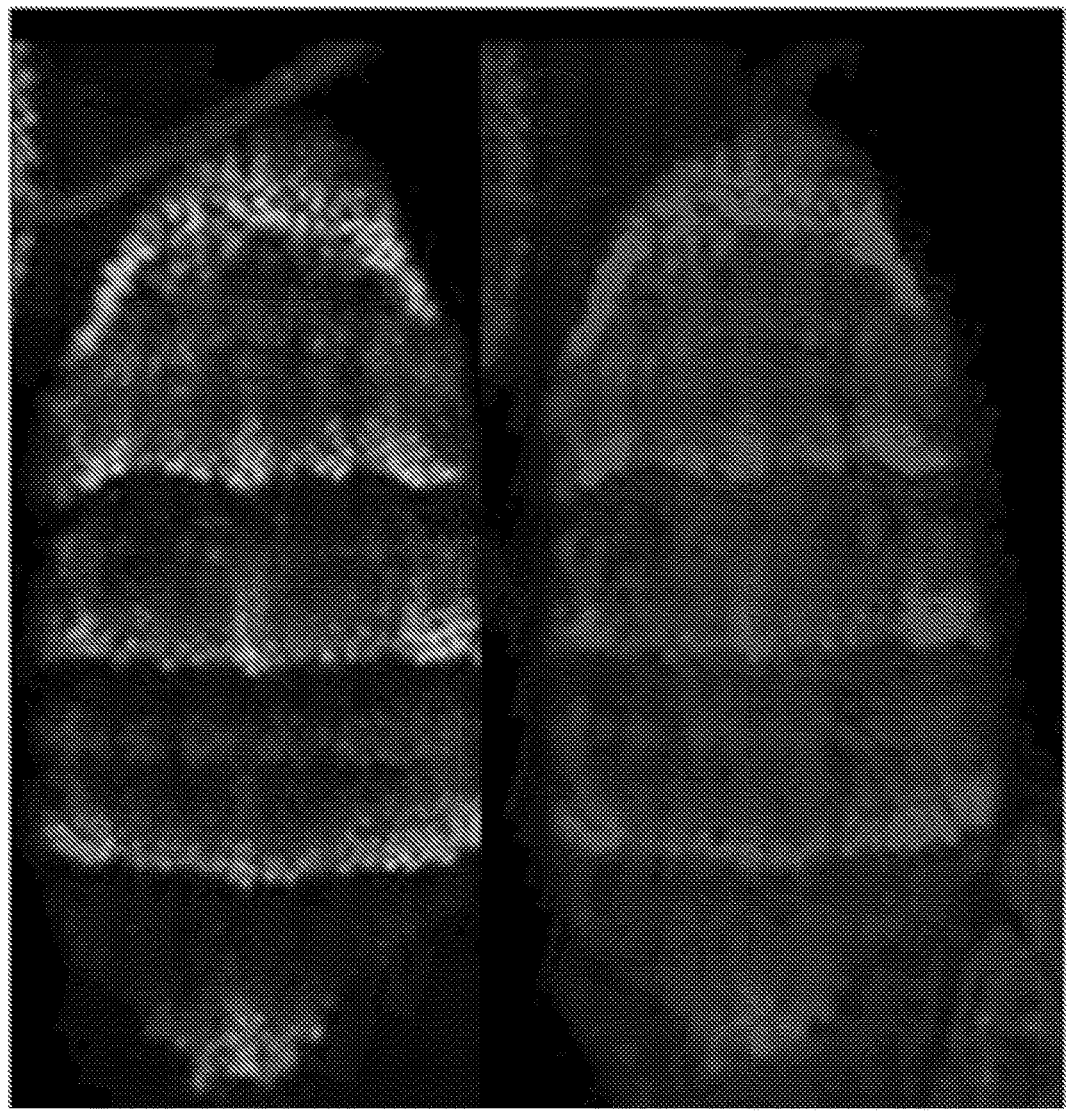
FIG. 15. ImmunoMUSE.
FIG. 15A. *Drosophila* embryo expressing a GFP fusion protein (shown in green).
FIG. 15B.

In various embodiments, the method further includes introduction of an additional at least two molecules, and a linker molecule including a nucleic acid sequence address complementary to one or more extension dendrites of the initial at least two molecules and a secondary trigger for the additional at least two molecules, wherein the additional at least two molecules and linker molecule are configured for self-assembled polymerization. In various embodiments, the initial at least two molecules and trigger are a first self-assembled polymerization, and introduction of the additional at least two molecules and a linker molecule are a second self-assembled polymerization. In various embodiments, the first and second self-assembled polymerization are a quadratic amplification. In other embodiments, the assembly includes a labeling polynucleotide complementary to an extension dendrite of the additional at least two molecules. For example, The use of extension dendrites 5 and/or 6 to seed additional polymers supports quadratic amplification as depicted in FIG. 6.

In various embodiments, self-assembling polymerization includes incubation of the at least two molecules, and trigger molecule for 1 min to 60 mins, 1 hour to 12 hours, 12-24 hours, 24 hours or more. In various embodiments, this includes incubation for 1, 2, 3, 4, 5, 5-10, 10-30, 30-60, 1-2 hours or 2 or more hours. In various embodiments, incubation is for 2 to 24 hours. In various embodiments, wherein a further linker molecule including an address complementary to one or more extension dendrites and a trigger for a further added at least two molecules, secondary incubation for the linker molecule, and further added at least two molecules is for 1 min to 60 mins, 1 hour to 12 hours, 12-24 hours, 24 hours or more. In various embodiments, this includes incubation for 1, 2, 3, 4, 5, 5-10, 10-30, 30-60, 1-2 hours or 2 or more hours. In various embodiments, incubation is for 2 to 24 hours.

Described herein is a method of polymerization, including adding at least two molecules, each including a nucleic acid and organic polymer, to a material including at least one trigger molecule including a nucleic acid, and triggering self-assembled polymerization, wherein each molecule includes one or more complementary sequences to another molecule. In other embodiments, the at least two molecules each comprise a nucleic acid hairpin, a nucleic acid stem, a binding dendrite, an extension dendrite. In other embodiments, the at least one nucleic acid trigger molecule includes an analyte binding agent. In other embodiments, the at least two molecules each comprise a nucleic acid hairpin, a nucleic acid stem, a nucleic acid dendrite includes a binding dendrite and extension dendrite, and an organic polymer, and further wherein the nucleic acid hairpin sequence of at least one first molecule is complementary to the nucleic acid binding dendrite sequence of at least one second molecule, and also wherein the nucleic acid hairpin sequence of the at least one second molecule is complementary to the nucleic acid binding dendrite sequence of the at least one first molecule, and the at least one nucleic acid trigger is coupled to an analyte binding agent, wherein the nucleic acid trigger is complementary to the nucleic stem and the binding dendrite of at least first one molecule.

In various embodiments, the material includes a substrate, such as a solid or liquid substrate. In various embodiment, the solid substrate includes glass, tissue culture surface, or any similar substrates known to one of ordinary skill. In various embodiments, the at least one trigger molecule is attached to the solid surface, such as a plurality of one of more trigger molecules deposited on the surface (e.g., array). In various embodiments, the at least one trigger molecule is dispersed within the liquid substrate.

In various embodiments, the material includes an analyte of interest. In various embodiments, the material is a biological specimen, including whole mount, tissue slices, one or more tissue and cells, etc. In various embodiment, the analyte of interest is bound to the analyte binding agent of the trigger molecule. In various embodiments, the biological specimen is deposited on the surface of a solid substrate. In various embodiment, the biological specimen is dispersed within a liquid substrate.

In other embodiments, the method includes generating a detectable signal by binding a labeling polynucleotide complementary to another molecule, wherein the labeling polynucleotide includes a labeling agent. In other embodiments, generating a detectable signal includes binding a labeling polynucleotide to an extension dendrite, wherein the labeling polynucleotide includes a labeling agent. In other embodiments, the method includes a labeling polynucleotide complementary to an extension dendrite of the initial at least two molecules, and/or additional at least two molecules. In various embodiments, the method includes two or more labeling polynucleotides, each of which is complementary to one or more extension dendrites of the initial at least two molecules and/or additional at least two molecules.

In various embodiments, the method is used in combination with detection and/or signal amplification, or both, of nucleic acid sequences in solutions. In various embodiments, the method is used in combination with detection and/or signal amplification, or both, of nucleic acid sequences in solid phase (ISH). In various embodiments, the method is used in combination with detection and/or signal amplification, or both, of small molecules in solutions. In various embodiments, the method is used in combination with detection and/or signal amplification, or both, of small molecules in solid phase. In various embodiments, the method is used in combination with detection and/or signal amplification, or both, of peptides and protein in solutions. In various embodiments, the method is used in combination with detection and/or signal amplification, or both, of peptides and protein in solid phase. In various embodiments, the method is used in combination with signal amplification from primary antibodies, such as ELISA and immunofluorescence. In various embodiments, the method is used in combination with signal amplification from secondary antibodies, such as ELISA and immunofluorescence.

Also described herein is a method including providing a sample containing an analyte of interest. In various embodiments, the method includes, adding at least two molecules, each molecule includes a nucleic acid and organic polymer, further adding a trigger molecule including a nucleic acid, and triggering polymerization, wherein each molecule includes one or more complementary sequences to another molecule. In other embodiments, the method includes a sample bound to a trigger, and adding at least two molecules, each molecule includes a nucleic acid and organic polymer, further adding a trigger molecule including a nucleic acid, and triggering polymerization, wherein each molecule includes one or more complementary sequences to another molecule.

In other embodiments, the at least two molecules each comprise a nucleic acid hairpin, a nucleic acid stem, a binding dendrite, an extension dendrite. In various embodiments, the polymer connects the nucleic acid stem to a dendrite. In other embodiments, the nucleic acid trigger includes an analyte binding agent. In other embodiments, the method includes generating a detectable signal by binding a labeling polynucleotide complementary to another molecule, wherein the labeling polynucleotide includes a labeling agent.

In various embodiments, the method further includes introduction of an additional at least two molecules, and a linker molecule including a nucleic acid sequence address complementary to one or more extension dendrites of the initial at least two molecules and a secondary trigger for the additional at least two molecules, wherein the additional at least two molecules and linker molecule are configured for self-assembled polymerization. In various embodiments, the initial at least two molecules and trigger are a first self-assembled polymerization, and introduction of the additional at least two molecules and a linker molecule are a second self-assembled polymerization. In various embodiments, the first and second self-assembled polymerization are a quadratic amplification. In other embodiments, the assembly includes a labeling polynucleotide complementary to an extension dendrite of the additional at least two molecules.

In other embodiments, the method includes generating a detectable signal by binding a labeling polynucleotide complementary to another molecule, wherein the labeling polynucleotide includes a labeling agent. In other embodiments, generating a detectable signal includes binding a labeling polynucleotide to an extension dendrite, wherein the labeling polynucleotide includes a labeling agent. In other embodiments, the method includes a labeling polynucleotide complementary to an extension dendrite of the initial at least two molecules, and/or additional at least two molecules. In various embodiments, the method includes two or more labeling polynucleotides, each of which is complementary to one or more extension dendrites of the initial at least two molecules and/or additional at least two molecules.

In various embodiments, the method includes generation of barcode sequences. In various embodiments, the method includes addition of a first oligonucleotide including an overhang sequence, signal label, and a sequence complementary to an extension dendrite, and introduction of a dsDNA oligonucleotide including a quencher label containing two overhangs, a first dsDNA overhang complementary to the overhang of the first oligonucleotide and a second dsDNA overhang. In various embodiments, the dsDNA oligonucleotide quencher label includes a short-distance quencher such as dabcyl and a fluorophore. In various embodiments, one or more dsDNA quencher labels can be hybridized to one another n times to generate a barcode.

In various embodiments, the method includes at least two oligonucleotides, including a label oligonucleotide and an eraser oligonucleotide. In various embodiments, the label oligonucleotide includes a first overhang sequence complementary to an extension dendrite and a second overhang sequence. In various embodiments, the eraser oligonucleotide a sequence complementary to the label oligonucleotide. In various embodiments, the method includes includes erasing by introducing the eraser oligonucleotide to an analyte labeled with the label oligonucleotide, washing away eraser-label dsDNA oligonucleotide dimer, and adding an additional label oligonucleotide. In various embodiments, the label-erase-label cycles is repeated n times to generate barcodes.

EXAMPLE 1

Molecular Mechanism

Figure 4:
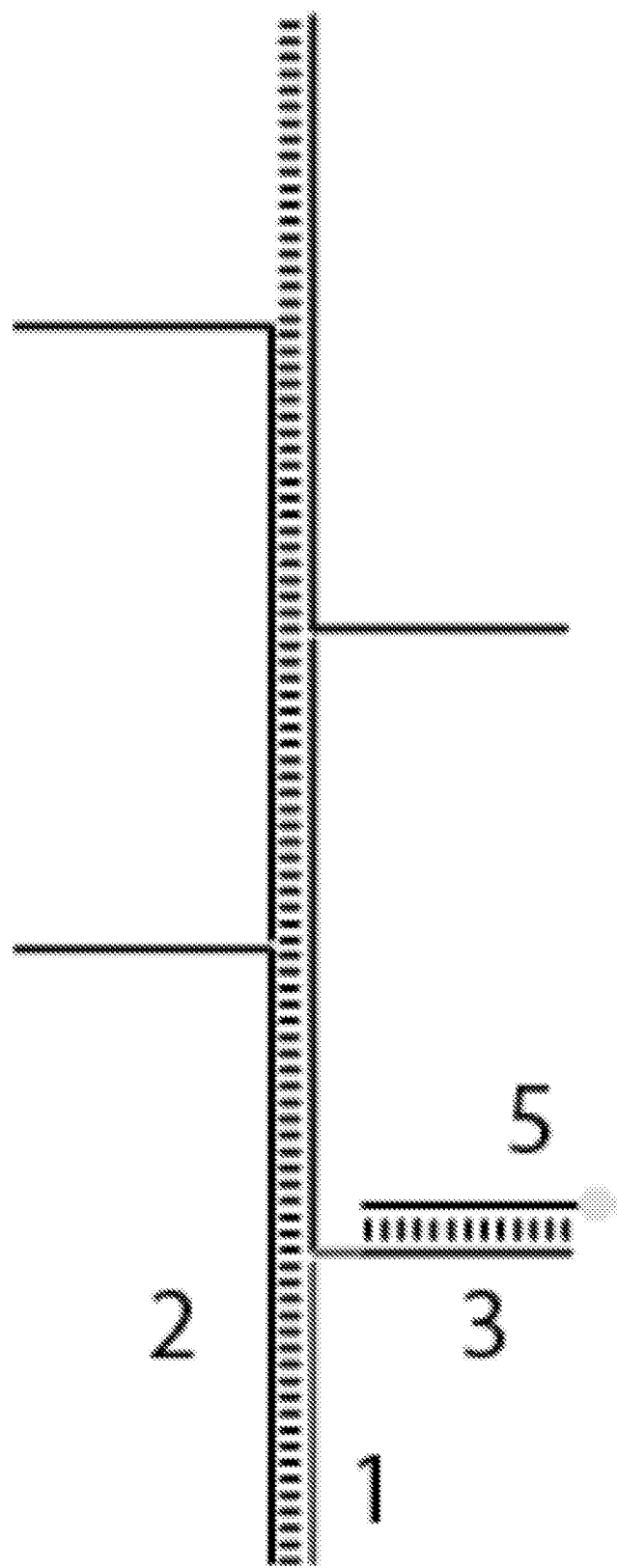
FIG. 4. Multi-modal dendrite attachment. Example of a direct attachment of a label (5) to a dendritic polymer (4) by hybridization to an extension dendrite (3). Note that each dendrite would eventually be labeled but only one is shown here for clarity. The label could comprise a fluorophore, quantum dot, chromogen, oligonucleotide, etc. Again, it is emphasized that the "labeling" step here is separated from the amplification, polymerization process of FIGS. 1 and 2.
Figure 5:
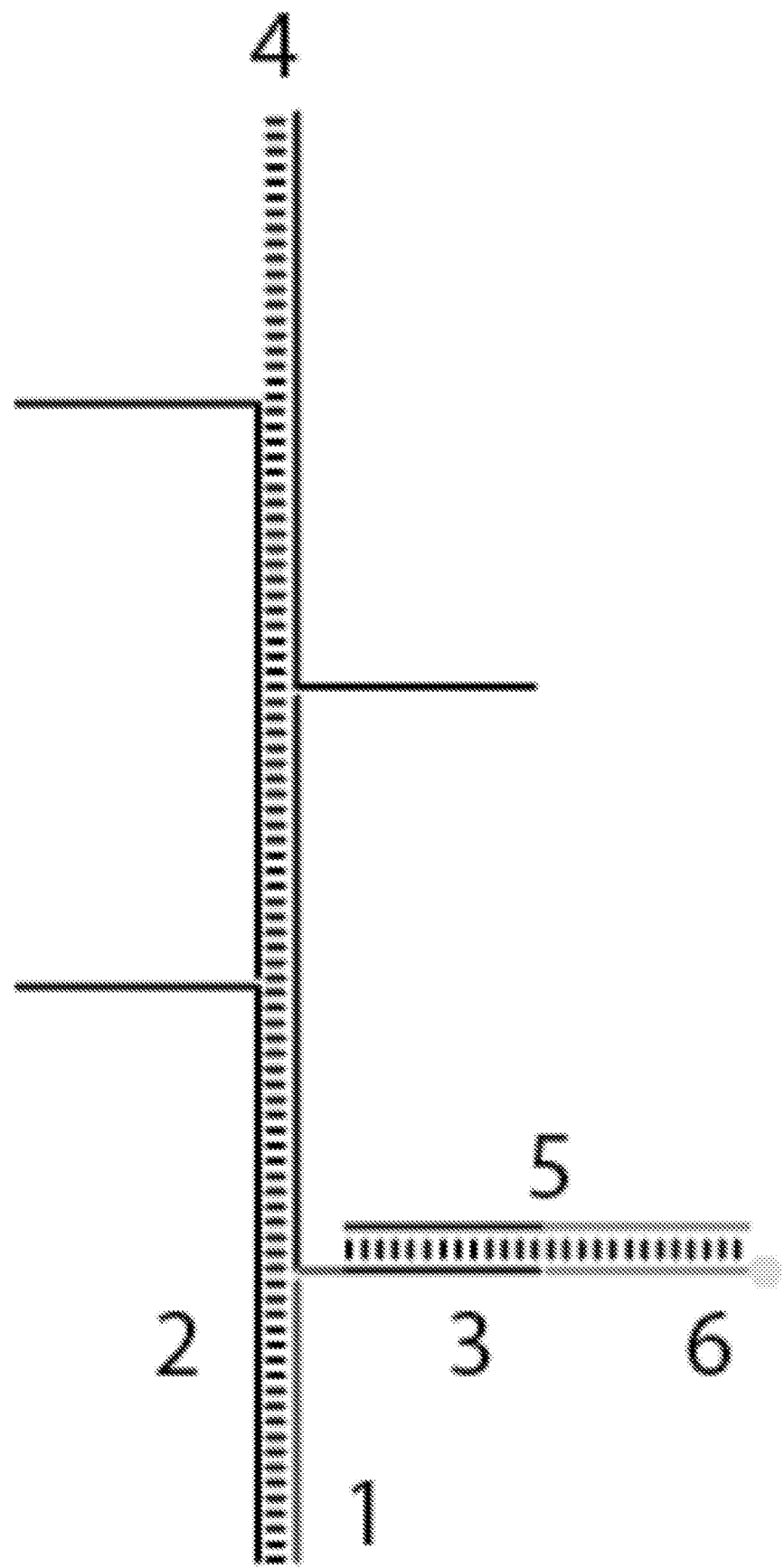
FIG. 5. Common-label strategy to reduce costs. In an variation of labeling approach, a linker oligonucleotide (5) composed of an "address" (a complementary sequence to the branch) and a label binding sequence (in green). This strategy results in significant cost savings as it requires only one type of labeled oligo (6) for any number of systems.

The Inventors' approach functions in the following way: a complementary pair of dendritic monomers can be used to generate a dendritic polymer by self-assembly, in a controllable manner, in the presence of the polymerization trigger by a chain reaction of nucleic acid hybridization and branch migration (FIGS. 1 and 2). The trigger can be used either directly or combined to an affinity ligand (FIGS. 3 and 4). The nature of the affinity ligand defines the type of analyte to be detected. Each dendrite of the polymer can be used to attach a label of choice such as a fluorophore, a quantum dot or a metal chelating polymer, for example (FIG. 5). Each dendritic polymer contains approximately two hundred dendrites. Hence, a large number of labels can be ultimately linked to the target of interest, dramatically multiplying its signal and rendering its detection rapid and unambiguous. After polymerization, the labeling can be done either by directly hybridizing a nucleic acid monomer to the dendrites (either prior to or after amplification) or by forming a nucleic acid duplex including a unique sequence, complementary to the target dendrite and a labeled nucleic acid monomer (FIG. 6). The second approach has the added advantage of dramatically diminishing the cost of multiplexed labeling since a single labeled nucleic acid monomer can be bound to any specific complementary label such that the number of expensive parts required is divided by the number of elements to be labeled simultaneously (FIG. 6). The potential to label and amplify the signal of a large number of ligands simultaneously at a relatively low cost is an important advantage of this approach compared to similar technologies such as HCR. The secondary label can also be employed to perform a quadratic amplification by adjoining a trigger sequence for a separate system. A key advantage of the approach is separation of the processes involved in analyte binding/labeling and signal amplification, as conventional techniques integrate or closely rely upon on the two steps.

EXAMPLE 2

Advantages

Another consideration: some fluorophores and other signal labels are not compatible with hairpin oligonucleotides due to secondary structure effects such as steric hindrance. A complementary probe label eliminates these effects and increases synthesis yield relative to direct attachment to a long oligonucleotide that can adopt secondary structures. In comparison to other methods that enable similar goals, the Inventors' approach has several advantages:

- By generating a dendritic polymer instead of a bare, directly labeled structure (as in HCR for example), the Inventors' approach provides much more flexibility and modularity in the nature of the labels that can be employed and whose signal will be amplified. This will enable users to choose the most appropriate label of choice, on a case specific basis. This provides flexibility to the user such that a variety of detection methods, which could be used orthogonally to the method described here to provide complementary information.
- In comparison to HCR, the Inventors' method significantly reduces costs by keeping the complexity of the hairpins low and enabling combinatorial use of labeled nucleic acid monomers to label a large variety of beacons.
- In comparison to a branched-DNA approach, the Inventors' method generates a dendritic DNA structure autonomously which relieves the user from having to perform several rounds of nucleic acid hybridization
- Traditional approaches are tedious and error-prone that renders this technique user-unfriendly.
- In comparison to branched-DNA the Inventors' method employs easier to synthesize components, which will result in significant savings and increased yield. In some instances, such as whole mount sample detection, the relatively small hairpin structures utilized, are superior in diffusion capability compared to larger structures, thereby providing signal generation advantages.
- In comparison to chromogen/tyramide approaches, this technology allows for a much larger degree of multiplexing. Further, since this technology relies on nucleic acid chemistry it is biocompatible and of minimal impact for the samples of interest. Hence, it is simpler and more allowing of parallel or sequential studies of the same samples such as immunohistochemistry, immunofluorescence, and nucleic acid sequencing.

EXAMPLE 3

Dendritic Amplifier Design Considerations

The described approach allows for an extremely large number of sequence designs for labeling combinations. For example, for a system with a 12 nucleotide long toehold/loop, 24 nucleotide long stem and 15 nucleotide long dendrite there are: $4^{12}*4^{24}*4^{12}*4^{15}=4^{63}=8.5*10^{37}$ possible sequences. This incredibly large design space provides the possibility to generate a very large number or orthogonal systems. The Inventors have established design criteria for generation of optimally amplifying systems.

For example, ideal sequence combinations meet certain design criteria including: minimization of alternative conformations to the preferred hairpin secondary structure, minimization of interactions between the toehold and the dendrite, and maximized stability of the stem. In more detail, the sequences are chosen to maximize base-stacking interactions in key positions such as the leading edge of the toehold, the last position of the toehold and the first two positions of the stem, within the stem in general, and at the leading edge of the dendrite. A variety of example sequences meeting these design criteria are shown.

EXAMPLE 4

Example Sequences for Self-Assembling Dendritic Polymerization Systems

```
System 1
Trigger 1
GTCCCACTCTCACCTCACCCGCACCATTTCATTTCC [SEQ ID
NO: 1]

Trigger 2
CCTTATCTATTCGTCCCACTCTCACCTCACCCGCAC [SEQ ID
NO: 2]

Monomer 1
GGAAATGAAATGGTGCGGGTGAGGTGAGAGTGGGACCCTTATCTATTCG

TCCCACTCTCACCTCACCCGCAC [SEQ ID NO: 3]-spacer-ACT

AACCCTAAACAC [SEQ ID NO: 4]

Monomer 2
CTCCACTCATACACC [SEQ ID NO: 5]-spacer-GTCCCACTCTC

ACCTCACCCGCACCATTTCATTTCCGTGCGGGTGAGGTGAGAGTGGGAC

GAATAGATAAGG [SEQ ID NO: 6]

System 2
Trigger1
CACCGTCCCATCCATCCCAGCCTCCAATACAATACC [SEQ ID
NO: 7]

Trigger2
CCTAATCAAATCCACCGTCCCATCCATCCCAGCCTC [SEQ ID
NO: 8]

Monomer1
GGTATTGTATTGGAGGCTGGGATGGATGGGACGGTGCCTAATCAAATCC

ACCGTCCCATCCATCCCAGCCTC [SEQ ID NO: 9]-spacer-ATC

TCATCTCATCCC [SEQ ID NO: 10]

Monomer2
TTCCACTTACTCCCG [SEQ ID NO: 11]-spacer-CACCGTCCCA

TCCATCCCAGCCTCCAATACAATACCGAGGCTGGGATGGATGGGACGGT

GGATTTGATTAGG [SEQ ID NO: 12]

System 3
Trigger 1
CTGCCTCACCTACTACCCTCGCTCCAAATCAAATCC [SEQ ID
NO: 13]

Trigger 2
CCTAAACTAATCCTGCCTCACCTACTACCCTCGCTC [SEQ ID
NO: 14]

Monomer 1
GGATTTGATTTGGAGCGAGGGTAGTAGGTGAGGCAGCCTAAACTAATCC

TGCCTCACCTACTACCCTCGCTC [SEQ ID NO: 15]-spacer-AC

CCTTACCTCTACC [SEQ ID NO: 16]

Monomer 2
CTCCATCCATCTCAC [SEQ ID NO: 17]-spacer-CTGCCTCACC

TACTACCCTCGCTCCAAATCAAATCCGAGCGAGGGTAGTAGGTGAGGCA

GGATTAGTTTAGG [SEQ ID NO: 18]

System 4
Trigger 1
CTCGCCCTTACACCTCACCCGCTCCTAAACTAAACC [SEQ ID
NO: 19]

Trigger 2
CCTTTACTTTACCTCGCCCTTACACCTCACCCGCTC [SEQ ID
NO: 20]

Monomer 1
GGTTTAGTTTAGGAGCGGGTGAGGTGTAAGGGCGAGCCTTTACTTTACC

TCGCCCTTACACCTCACCCGCTC [SEQ ID NO: 21]-spacer-AT

TCCCATACTCTTC [SEQ ID NO: 22]

Monomer 2
CTTCCAATCATCCCG [SEQ ID NO: 23]-spacer-CTCGCCCTTA

CACCTCACCCGCTCCTAAACTAAACCGAGCGGGTGAGGTGTAAGGGCGA

GGTAAAGTAAAGG [SEQ ID NO: 24]

System 5
Trigger 1
CTGCCTCACCTCCAACTCCCGCTCCTATTCATTTCC [SEQ ID
NO: 25]

Trigger 2
CCTTTACTATTCCTGCCTCACCTCCAACTCCCGCTC [SEQ ID
NO: 26]
```

Monomer 1
GGAAATGAATAGGAGCGGGAGTTGGAGGTGAGGCAGCCTTTACTATTCC

TGCCTCACCTCCAACTCCCGCTC [SEQ ID NO: 27]-spacer-AC

ACTCTACAACTAC [SEQ ID NO: 28]

Monomer 2
CCAATCAATCCCTAC [SEQ ID NO: 29]-spacer-CTGCCTCACC

TCCAACTCCCGCTCCTATTCATTTCCGAGCGGGAGTTGGAGGTGAGGCA

GGAATAGTAAAGG [SEQ ID NO: 30]

System 6
Trigger 1
CACCGACCATCCATACACCGCCACCTTTACATTTCC [SEQ ID

NO: 31]

Trigger 2
CCTTTACTATTCCACCGACCATCCATACACCGCCAC [SEQ ID

NO: 32]

Monomer 1
GGAAATGTAAAGGTGGCGGTGTATGGATGGTCGGTGCCTTTACTATTCC

ACCGACCATCCATACACCGCCAC [SEQ ID NO: 33]-spacer-TC

ACTAACTAAACTC [SEQ ID NO: 34]

Monomer 2
TTCAATCATCACCAG [SEQ ID NO: 35]-spacer-CACCGACCAT

CCATACACCGCCACCTTTACATTTCCGTGGCGGTGTATGGATGGTCGGT

GGAATAGTAAAGG [SEQ ID NO: 36]

System 7
Trigger 1
CAGCCTCACCATAACATCACCGACCTAAACTAAACC [SEQ ID

NO: 37]

Trigger 2
CCTTTACATTTCCAGCCTCACCATAACATCACCGAC [SEQ ID

NO: 38]

Monomer 1
GGTTTAGTTTAGGTCGGTGATGTTATGGTGAGGCTGCCTTTACATTTCC

AGCCTCACCATAACATCACCGAC [SEQ ID NO: 39]-spacer-AA

TCCAATCACATCC [SEQ ID NO: 40]

Monomer 2
CTTCAATCTCACCCG [SEQ ID NO: 41]-spacer-CAGCCTCACC

ATAACATCACCGACCTAAACTAAACCGTCGGTGATGTTATGGTGAGGCT

GGAAATGTAAAGG [SEQ ID NO: 42]

System 8
Trigger 1
CTCCGACCTCTACTACCCTGCCTCCATAACAATTCC [SEQ ID

NO: 43]

Trigger 2
CCAAATCTAAACCTCCGACCTCTACTACCCTGCCTC [SEQ ID

NO: 44]

Monomer 1
GGAATTGTTATGGAGGCAGGGTAGTAGAGGTCGGAGCCAAATCTAAACC

TCCGACCTCTACTACCCTGCCTC [SEQ ID NO: 45]-spacer-AC

CCTACTCTCACTC [SEQ ID NO: 46]

Monomer 2
TCACTTATACTCCTG [SEQ ID NO: 47]-spacer-CTCCGACCTC

TACTACCCTGCCTCCATAACAATTCCGAGGCAGGGTAGTAGAGGTCGGA

GGTTTAGATTTGG [SEQ ID NO: 48]

System 9
Trigger 1
CAGCCACTTTCACCATACACCGACCTTTACTTTACC [SEQ ID

NO: 49]

Trigger 2
CCAAATCAATACCAGCCACTTTCACCATACACCGAC [SEQ ID

NO: 50]

Monomer 1
GGTAAAGTAAAGGTCGGTGTATGGTGAAAGTGGCTGCCAAATCAATACC

AGCCACTTTCACCATACACCGAC [SEQ ID NO: 51]-spacer-AA

TCCCAATCCAAAC [SEQ ID NO: 52]

Monomer 2
CTTTCATACTACTCC [SEQ ID NO: 53]-spacer-CAGCCACTTT

CACCATACACCGACCTTTACTTTACCGTCGGTGTATGGTGAAAGTGGCT

GGTATTGATTTGG [SEQ ID NO: 54]

System 10
Trigger 1
CTCGCCCACTCACCTCACCCGCACCTTATCATTTCC [SEQ ID

NO: 55]

Trigger 2
CCAAATCAAATCCTCGCCCACTCACCTCACCCGCAC [SEQ ID

NO: 56]

Monomer 1
GGAAATGATAAGGTGCGGGTGAGGTGAGTGGGCGAGCCAAATCAAATCC

TCGCCCACTCACCTCACCCGCAC [SEQ ID NO: 57]-spacer-TA

CCCTAACCTCTAC [SEQ ID NO: 58]

Monomer 2
CCTTTACTACTCCCG [SEQ ID NO: 59]-spacer-CTCGCCCACT

CACCTCACCCGCACCTTATCATTTCCGTGCGGGTGAGGTGAGTGGGCGA

GGATTTGATTTGG [SEQ ID NO: 60]

System 11 10 toehold -15 stem -12 dendrite
initiator 1
CACGCTCCACTCCACCTAACTAACC [SEQ ID NO: 61]

initiator 2
CCATACATACCACGCTCCACTCCAC [SEQ ID NO: 62]

hairpin 1
GGTTAGTTAGGTGGAGTGGAGCGTGCCATACATACCACGCTCCACTCCA

C [SEQ ID NO: 63]-spacer-ATCATCTCATCC [SEQ ID

NO: 64]

-continued

```
hairpin 2
CCTAAATCTCTA [SEQ ID NO: 65]-spacer-CACGCTCCACTCC
ACCTAACTAACCGTGGAGTGGAGCGTGGTATGTAT [SEQ ID
NO: 66]

System 12 8 toehold -10 stem -18 dendrite
initiator 1
ATCGCCTAGCCTTAATCC [SEQ ID NO: 67]

initiator 2
CCTTTATCATCGCCTAGC [SEQ ID NO: 68]

hairpin 1
AACGCCAACCCAAATACC [SEQ ID NO: 69]-spacer-ATCGCCT
AGCCTTAATCCGCTAGGCGATGATAAAGG [SEQ ID NO: 70]

hairpin 2
GGATTAAGGCTAGGCGATCCTTTATCATCGCCTAGC [SEQ ID NO:
71]-spacer-CCTATTTCAACGCCAACC [SEQ ID NO: 72]

System 13 6 toehold -10 stem -16 dendrite
initiator 1
AACCCGAACCTAAAGC [SEQ ID NO: 73]

initiator 2
GCTTTAAACCCGAACC [SEQ ID NO: 74]

hairpin 1
GCTTTAGGTTCGGGTT [SEQ ID NO: 75]-spacer-GCTTTAAAC
CCGAACCATACCCACACCAACCC [SEQ ID NO: 76]

hairpin 2
CCCAACCACCACCAATAACCCGAACCTAAAGC [SEQ ID NO: 77]-
spacer-GGTTCGGGTTTAAAGC [SEQ ID NO: 78]

System 14 6 toehold -8 stem -10 dendrite
initiator 1
CGCCACCCTAAACC [SEQ ID NO: 79]

initiator 2
CCATTTCGCCACCC [SEQ ID NO: 80]

hairpin 1
GGTTTAGGGT [SEQ ID NO: 81]-spacer-GGCGCCATTTCGCCA
CCCATCTCTTCCC [SEQ ID NO: 82]

hairpin 2
CCCTCTACTACGCCACCCTAAACCGGGT [SEQ ID NO: 83]-
spacer-GGCGAAATGG [SEQ ID NO: 84]
```

EXAMPLE 5

Exemplary Labeling Technique: *Drosophila* Embryo Protocol

An exemplary technique for labeling *Drosophila* embryos is described herein. Starting from embryos fixed in 4% PFA and stored in methanol at −20°, samples are manipulated as follows.

1. Rehydrate
   a. 80% Methanol in PBS 5 mins
   b. 50% Methanol in PBS 5 mins
   c. 25% Methanol in PBS 5 mins
2. ProK Treatment
   a. Incubate 13 min in 3 µg/ml ProK in PBST.
   b. Transfer 1 h on ice.
   c. Block proK with 2 mg/ml Glycine for 2 min.
   d. Repeat glycine block.
   e. Rinse 2× with PBST
   f. Wash 3×5 min in PBST
3. Post-Fixation
   a. Fix in 4% PFA in PBST 20 min. with shaking.
   b. Wash 3×5 min in PBST
4. Probe Hybridization
   a. Add 100 µl of preheated (45°) hybridization buffer
   b. Incubate for 30 minutes at 45°
   c. Prepare probe solution by adding 0.1 µl (0.5 pM) of each 1 µM probe stock to 100 µl of preheated (45°) hybridization buffer.
   d. Remove "pre-hybridization" buffer
   e. —samples could be stored here (1-2 weeks).
   f. Add 100 µl of hybridization buffer+probes prepared above
   g. Incubate 4 hours or overnight at 45°
   h. Wash with preheated (45°) wash buffer
      i. 4×15 minutes
5. Generation of Dendritic Polymers
   a. During last washing step above, start snap cooling:
      i. Place 2 µl of each hairpin solution in a separate eppi.
      ii. Melt at 95 degrees for 90 seconds
      iii. Place in a drawer for 30 minutes at RT°
      iv. During this time, change wash buffer with 100 µl of amplification buffer. Keep at RT°
      v. Remove "pre-amplification" buffer (after at least 10 minutes)
      vi. Add 100 µl of RT° amplification buffer to H1 than transfer to H2 and finally, to sample.
      vii. Incubate for 1 hour or up to overnight at RT°, protect from light
      viii. Wash with 5×SSCT
         1. 2×5 minutes
         2. 2×30 minutes
6. Labeling
   i. Add 1 pmole of label in 100 µl 5×SSCT.
   ii. Hybridize for 1 hour at RT °
   iii. Wash 4×15 min. in 5×SSCT
7. Mount and Image.

II. FFPE Slides Protocol

1. Paraffin Removal
Add 500 µl xylene 3 mins
Add 500 µl xylene 3 mins
Add 500 µl 1:1 Xylene ethanol 3 mins
Wash with 500 µl ethanol 3 mins
Wash with 500 µl ethanol 3 mins
2. Rehydration
95% ethanol 3 mins
70% ethanol 3 mins
50% ethanol 3 mins
PBST 3 mins
PBST 3 mins
3. Proteinase K Digestion
Immerse slide in 10 µg/mL of proteinase K solution for 40 min at 37°.
Wash slide 2×3 min at room temperature in PBST.
4. Prehybridization
Pre-warm two humidified chambers with one at 45° and the other one at 65°.
Dry slide by blotting edges on a Kimwipe.
Add 400 µL of probe hybridization buffer on top of the tissue sample.
Pre-hybridize for 10 min inside the 65° humidified chamber.
Prepare probe solution by adding 0.2 pmol of each probe (1 µL of 1 µM stock per probe) to 100 µL of probe hybridization buffer at 45° Remove the pre-hybridization solution and drain excess buffer on slide by blotting edges on a Kimwipe. Add 400 µL of the probe solution on top of the tissue sample. Place a coverslip on the tissue sample and incubate for 2-4 hours or overnight in the 45° humidified chamber.
Wash 4× in 45° wash buffer 1 ml
5. Wash Probes
4×15 minute washes with wash buffer pre-warmed at 45°
Wash twice with 5×SSCT
6. Prepare Monomers:
2 ul of hairpin 1 and 2 are required per 100 ul of reaction volume.
Snap cool: 3 minutes at 95°→3 minutes on ice→25 minutes at RT°
7. Pre-Amplification
Add 400 µl of Amplification buffer, 10 minutes at RT
Blot away pre-amp buffer.
Add hairpins in amplification buffer
Incubate 1 hour up to overnight at RT°.
8. Wash Monomers
4×15 minute washes with 5×SSCT at RT°.
Add label 1 pmole of label.
Hybridize for 1 hour.
4×15 minute washes with 5×SSCT at RT°.
9. Mount and Image III. Antibody Amplification Protocol Proceed with normal antibody staining protocol until after primary antibody washes in PBST.
1. Prepare Monomers:
2 ul of monomers 1 and 2 are required per 100 ul of reaction volume.
Snap cool each 2 µl of monomer separately.
Snap cool: 3 minutes at 95°→3 minutes on ice→25 minutes at RT°
2. Amplification
Mix monomers with appropriate amount of 5×SSCT.
Add appropriate amount of pre-prepared monomers in 5×SSCT to sample.
Incubate 1 hour up to overnight at RT°.
3. Wash Monomers
4×15 minute washes with 5×SSCT at RT°.
Add label 1 pmole of label.
Hybridize for 1 hour.
4×15 minute washes with 5×SSCT at RT°.
4. Mount and Image
Buffers:
5×SSCT—750 mM Sodium Chloride, 75 mM Trisodium Citrate, 0.1% Tween 20, 1 liter of double-distilled water.
Buffers:
5×SSC—750 mM Sodium Chloride, 75 mM Trisodium Citrate, 0.1% Tween 20 1 liter of double-distilled water.
5×SSCT
5×SSC—0.1% Tween 20
Hybridization buffer—50% formamide, 5×SSC, 9 mM Citric acid (pH 6), 50 µg/mL heparin, 1×Denhardt's solution, 10% Dextran sulfate, 0.1% Tween 20.
Wash buffer—50% formamide, 5×SSC, 9 mM Citric acid (pH 6), 50 µg/mL heparin, 0.1% Tween 20.
Amplification buffer—5×SSCT, 10% Dextran Sulfate.

EXAMPLE 6

Barcode Labeling Approaches

The multi-modal design allows exploitation of different labeling agents, including further variations of labeling techniques which themselves incorporate combinatorial approaches. For example, sequential barcoding approaches enable the generation of $S^n$ barcoded, where S is the number of different signal species (ex. fluorophores emitting in different wavelengths) and n is the number of sequential labeling runs.

The dendritic polymers can be used to generate barcode sequences. The Inventors have devised two approaches that improve on traditional methods by enabling the rapid and ambient temperature exchange of fluorescent labels in buffers that are gentle to the samples being studied. In the label-quench-label technique, a first oligonucleotide complementary to a dendrite sequence on the dendritic polymer to label that contains an additional 15 nucleotide "overhang" sequence, constitutes the first barcode label. The "overhang" serves to anchor a dsDNA "quencher" label containing two overhangs, one complementary to the overhang of the first label and a second that will serve to anchor the next label. The "quencher" label oligonucleotide contains a short-distance quencher such as dabcyl and a fluorophore. The hybridization of the quencher label to the overhang of the previous label places the quencher and the previous fluorophore in very clos distance such that the fluorescence of the first fluorophore is quenched and only the fluorophore contained on the "quencher" label can emit a signal. In this manner, subsequent "quencher" labels can be hybridized to one another n times to generate a barcode.

The label-erase-label approach requires two oligonucleotide species. The label is complementary to a dendrite and includes a 12 base pair overhang. The eraser is fully complementary to the label, including the 12 base pair overhang. To initiate a label replacement, an eraser oligonucleotide is added to a previously labeled sample. The hybridization of the eraser to the overhang of the label will trigger a branch-migration event such that an eraser-label dsDNA oligonucleotide dimer will be generate as the label detached from the dendrite. The eraser-label dimer can then be washed away. Finally, a new label is added to the sample. These label-erase-label cycles can be repeated n times to generate barcodes. In comparison to the label-quench-label approach, this method is simpler and cheaper.

EXAMPLE 7

Additional Protocols

As described, MUSE includes three constituent steps: detection, amplification and labeling. Detection is usually performed as customary for the analyte in question (e.g. in situ hybridization for DNA and RNA analytes, immunohistochemistry for proteins and peptides) and the type of sample being studied. Following detection of analytes, a common amplification process involving self-assembly of nucleic acid monomers. MUSE is compatible with different labels of choice; the labeling protocols will therefore vary depending on the type of label being used. Additional detection, amplification and labeling protocols below, as well as representative results.

EXAMPLE 8

Detection Protocols

Detection protocols are independent from the MUSE amplification and labeling steps. For compatibility, the only requirement is for the samples to be in a compatible buffer (ex. 5×SSCT, PBS) prior to the MUSE amplification step.

Below are examples of detection protocols for DNA, RNA and Protein detection.

EXAMPLE 9

DNA In Situ Hybridization on FFPE Slides

1. Incubate in 2×SSCT+50% formamide for 3 min. at 92° C.
2. Transfer to a coplin jar with 2×SSCT+50% formamide at 60° C.
3. Incubate for 20 min.
4. Remove slides and allow to cool to RT°.
5. Add 25 µl of a hybridization buffer composed of 2×SSCT, 50% formamide, 10% (w/v) dextran sulfate, 10 µg RNase A, and 10-20 pmole of probes
6. Cover with a coverslip and seal with rubber cement.
7. Allow the rubber cement to air-dry for 5' at room temperature
8. Denature for 3 min. at 92° C.
9. Transfer slides to a humidified chamber. Hybridize overnight at 37° C.
10. Remove coverslip and wash slides in a pre-warmed coplin jar with 2×SSCT at 60° C. for 15 min.
11. Transfer to a coplin jar containing 2×SSCT at RT° and
12. Incubate for 10 min.
13. Transfer slides to a coplin jar containing 0.2×SSC at room temperature and
14. Incubate for 10 min.
15. Blot slide edges on filter paper to remove most buffer. Do not allow slide to dry.
16. Add mounting medium and mount.

EXAMPLE 10

RNA In Situ Hybridization on *Drosophila* Embryo 1. 80% Methanol in PBS 5 mins
2. 50% Methanol in PBS 5 mins
3. 25% Methanol in PBS 5 mins
4. Incubate 13 min in 3 µg/ml ProK in PBST
5. Transfer 1 h on ice
6. Block proK with 2 mg/ml Glycine for 2 min
7. Repeat
8. Rinse 2× with PBST
9. Wash 3×5 min in PBST
10. Post fixation
11. Fix in 4% PFA in PBST 20 min. with shaking
12. Wash 3×5 min in PBST
13. Add 100 µl of preheated (45° C.) hybridization buffer
14. Incubate for 30 min at 45° C.
15. Prepare probe solution by adding 0.1 µl (0.5 pM) of each 1 µM probe stock to 100 µl of preheated (45 C) hybridization buffer
16. Remove "pre-hybridization" buffer
17. Add 100 µl of hybridization buffer+probes prepared above
18. Incubate overnight at 45° C.
19. Wash 4 time with preheated (45° C.) wash buffer
20. Add 1 mL 5×SSCT

EXAMPLE 11

RNA In Situ Hybridization on Ffpe Slides

1. Add 500 µl xylene 3 mins
2. Add 500 µl xylene 3 mins
3. Add 500 µl 1:1 Xylene ethanol 3 mins
4. Wash with 500 µl ethanol 3 mins
5. Wash with 500 µl ethanol 3 mins
6. Wash with 500 µl 95% ethanol 3 mins
7. Wash with 500 µl 70% ethanol 3 mins
8. Wash with 500 µl 50% ethanol 3 mins
9. Wash with 500 µl PBST 3 mins
10. Wash with 500 µl PBST 3 mins
11. Immerse slide in 2 µg/mL of proteinase K solution for 40 min at 37° C.
12. Wash slide 2×3 min at room temperature in PBST
13. Dry slide by blotting edges on a Kimwipe
14. Add 400 µL of probe hybridization buffer on top of the tissue sample
15. Pre-hybridize for 10 min inside the 45° C. humidified chamber.
16. Prepare probe solution (use 1 µl of 1 µM probe mix)
17. Remove the pre-hybridization solution and drain excess buffer on slide by blotting edges on a Kimwipe
18. Add 100 µL of the probe solution on top of the tissue sample.
19. Place a coverslip on the tissue sample and incubate 4 hours in the 45° C. humidified chamber.
20. 4×15 minute washes with wash buffer pre-warmed at 45° C.
21. Wash 2× with 5×SSCT

EXAMPLE 12

Immunofluorescence Conjugation Strategies

Antibody/affinity ligands can be conjugated to ssDNA MUSE triggers in a variety of ways including for example, amino, maleimide and bis-sulfone crosslinkers.

Conjugation Protocol (Bis-Sulfone-PEG4-DBCO, Ex.)
1. Prepare PBS+10 mM EDTA
2. Buffer exchange 200 µg Pan Ras antibody into PBS-EDTA 2× in 100 KDA column
3. Resuspend in 70 µl PBS+EDTA
4. Keep 10 µl for controls
5. Use 10× excess of TCEP
6. Add appropriate amount of TCEP 1 mM to the antibody.
7. Reduce the antibody for 1 hour at RT°
8. Buffer exchange antibody 2 times in amicon 50 in PBS+10 mM EDTA.
9. Resuspend in 60 µl PBS+10 mM EDTA
10. Add 5 fold molar excess of Bis-Sulfone-PEG4-DBCO reagent
11. Mix well by pipetting.
12. Incubate at RT° overnight.
13. Buffer exchange into PBS 3× in 30 KDa columns.
14. Resuspend in 50 µl PBS.
15. Keep 25 µl for controls.
16. Use 2 fold excess of oligo-azyde in PBS.
17. Incubate overnight at 4° C.
18. Buffer exchange in PBS 3× in 30 KDa columns.
19. Recover in 100 µl PBS

EXAMPLE 13

Immunostaining Protocol

Immunostainings can be performed in any preferred way by the user, as long as the final washes are in PBS.
1. Incubate sample with appropriate dilution of primary antibody for two hours at RT° (or 4° C. overnight).

2. Wash 3×10 minutes in PBS+0.1% Tween-20.
3. Block 30 minutes in 3% Heat Inactivated Goat Serum
4. Incubate 1 hour at RT° with appropriate concentration of secondary antibody (usually 1/500).
5. Wash 3×10 minutes in PBS.

EXAMPLE 14

Amplification Protocol

For the reasons described, a common amplification process is utilized involving self-assembly of nucleic acid monomers.
1. Denature MUSE hairpins (2 µl/100 µl of reaction solution) for 3 minutes at 95° C.
2. Place 10 minutes on ice.
3. Place 20 minutes at RT°.
4. Mix hairpins with amplification mix.
5. Place on previously hybridized on immunostained sample.
6. Let amplify overnight at RT°
7. Wash 4×15 minutes in 5×SSCT

EXAMPLE 15

Labeling Protocols—Fluorescent

Fluorescent label conjugation strategies Fluorophores can be conjugated to the oligonucleotides in variety of ways including (but not exhaustive), amino, maleimide or click mediated conjugation. An exemplary conjugation protocol is provided:
Label Possibilities
One can use ssDNA oligonucleotides conjugated to a fluorophore as labels. However, it is also possible to use dsDNA labels containing up to 4 fluorophores (at each 5' 3' end) to enhance the signal further.
Fluorophore Labeling Protocol
Starting from ISH or IF:
1. Add 2 µl of Fluorophore labels per 100 µl of hybridization solution.
2. Hybridize for 2 hours at RT in hybridization buffer.
3. Wash 2×15 minutes in 5×SSCT.
4. Wash 2×15 minutes in PBS.
5. Mount and Image.

EXAMPLE 16

Labeling Protocols—Quantum Dot

Quantum Dot Conjugation Strategy
Quantum dots can be conjugated to the oligonucleotides in variety of ways. An exemplary conjugation protocol is provided:
Quantum Dot Labeling Protocol
1. Starting from ISH or IF:
2. Add 2 µl of Quantum Dot labels per 100 ul of hybridization solution.
3. Hybridize for 2 hours at RT.
4. Wash 2×15 minutes in 5×SSCT.
5. Wash 2×15 minutes in PBS.
6. Mount and Image.

EXAMPLE 17

Labeling Protocols—Elemental

Elemental Label Conjugation Strategy
The elemental labels are generated by conjugating a Metal Chelating Polymer (Fluidigm Corp.) to an oligonucleotide containing a thiol or dithiol moiety via maleimide chemistry. A protocol for the conjugation can be found below.
Elemental Label Generation Protocol
1. Resuspend oligo in TE buffer to 200 µM
2. Mix: 50 µL of (20 µM) oligo to 20 µl TE buffer
3. Add 30 µl of 0.5M TCEP
4. Let stand at least two hours at RT°.
5. —Pre-load the MCP with pure isotope—
6. Wait 30 mins after step II.
7. Quickly spin-down polymer tube for 10 s.
8. Resuspend polymer with 95 µL of L-Buffer.
9. Mix well by pipetting.
10. Add 5 µL of isotope solution (2 mM total).
11. Mix well by pipetting.
12. Incubate at 37° C. for 30-40 min.
13. After 35 minutes:
14. Add 200 µL of L-Buffer to the 3K UF columns.
15. Add the isotope loaded MCP solution to 3K UF columns containing the L-Buffer.
16. Spin for 25 min. at full speed at RT°.
17. Add 300 µL of C-Buffer to the 3K UF columns.
18. Spin for 30 min. at full speed at RT°.
19. —Recover reduced Dithiol-oligos—
20. SIMULTANEOUSLY WITH STEP 15 USE 1 CENTRIFUGE
21. Add 300 L of C-Buffer to 3K UF columns.
22. Add reduced Dithiol-oligos in TCEP to 3K UF columns.
23. Spin for 15 min. at full speed at RT°.
24. Add 300 µL of C-Buffer to 3K UF columns.
25. Spin for 20 min. at full speed at RT°.
   —Retrieve the loaded MCP and the reduced Dithiol-oligos—
26. Retrieve the 3K UF columns containing the purified isotope loaded MCP.
27. Retrieve the 3K UF columns containing the purified reduced Dithiol-oligos.
   —Conjugate the loaded MCP with the reduced Dithiol-oligos—
28. Resuspend the loaded MCPs in the 3K UF columns in 60 µL of C-Buffer.
29. Mix well by pipetting.
30. Transfer the loaded MCPs in C-Buffer into the 3K UF columns containing the reduced Dithiol-oligos.
31. Incubate for 2 hours at 37°.
32. Add 5 mM of TCEP (1 ul of 0.5M TCEP).
33. Incubate 30 more minutes.
34. Transfer the loaded MCPs and reduced Dithiol-oligos in C-Buffer into the 10K UF columns containing the reduced Dithiol-oligos.
   Wash the isotope conjugated oligos
35. Add 300 µL of W-Buffer to the 10K UF columns containing the MCPs.
36. Spin for 10 min. at full speed at RT°.
37. Wash 4 times with 500 ul ultrapure water.
   —Recover the MCPs—
38. Add 30 µL of 5×SSCT to the 10K UF columns containing the MCPs.
39. Rinse the walls of the UF columns.
40. Invert UF column into a new collection tube.

41. Spin for 2 min. at 1000 Gs.
42. Repeat once.
43. Measure with Qubit ssDNA kit
44. Prepare 1 uM stock Elemental Labeling Protocol
1. Starting from an ISH or IHC,
2. Add 2 µl of elemental labels per 100 ul of hybridization solution.
3. Hybridize for 2 hours at RT.
4. Wash 2×15 minutes in 5×SSCT.
5. Wash 2×15 minutes in PBS.
6. Quickly rinse in ddH2O
7. Air dry
8. Image with a Fluidigm Hyperion unit or a nanoSIMS setup adapted for MIBI.

EXAMPLE 18

Quadratic Amplification

Quadratic amplifications can be performed to further amplify the signal of nucleic acid in situ hybridization and immunohistochemistry assays.

Quadratic Amplification Protocol
1. Denature MUSE hairpins (2 µl/100 µl of reaction solution) for 3 minutes at 95° C.
2. Place 10 minutes on ice.
3. Place 20 minutes at RT°.
4. Mix hairpins with amplification mix.
5. Place on previously hybridized on immunostained sample.
6. Let amplify overnight at RT°
7. Wash 4×15 minutes in 5×SSCT
8. Mix 2 µl of quadratic adaptors with 100 µl of hybridization solution.
9. Hybridize 2 hours at RT°
10. Wash 4×15 minutes in 5×SSCT
11. During washes, repeat hairpin formation for secondary amplification system (steps 1-4).
12. Let amplify overnight at RT°
13. Wash 4×15 minutes in 5×SSCT
14. Mix 2 µl of label with 100 µl of hybridization solution.
15. Hybridize 2 hours at RT°
16. Wash 2×15 minutes in 5×SSCT
17. Wash 2×15 minutes with PBS.
18. Mount and image.

EXAMPLE 19

Barcodes

Spectral Barcode
Spectral barcodes employ two different labels per amplification system (ex: Muse1A alexa488+Muse1B alexa594) to generate 52 combinations with 5 fluorophores, for example. For spectral barcodes, it is necessary to proceed as with fluorophore labels (described previously).

Sequential Barcodes
Sequential barcoding approaches enable the generation of Sn barcoded, where S is the number of different signal species (ex. fluorophores emitting in different wavelengths) and n is the number of sequential labeling runs.

The dendritic polymers can be used to generate barcode sequences. The Inventors have devised two approaches that improve on published methods by enabling the rapid and ambient temperature exchange of fluorescent labels in buffers that are gentle to the samples being studied.

In the label-quench-label technique, a first oligonucleotide complementary to a dendrite sequence on the dendritic polymer to label that contains an additional 15 nucleotide "overhang" sequence, constitutes the first barcode label. The "overhang" serves to anchor a dsDNA "quencher" label containing two overhangs, one complementary to the overhang of the first label and a second that will serve to anchor the next label. The "quencher" label oligonucleotide contains a short-distance quencher such as dabcyl and a fluorophore. The hybridization of the quencher label to the overhang of the previous label places the quencher and the previous fluorophore in very close distance such that the fluorescence of the first fluorophore is quenched and only the fluorophore contained on the "quencher" label can emit a signal. In this manner, subsequent "quencher" labels can be hybridized to one another n times to generate a barcode.

The label-erase-label approach requires two oligonucleotide species. The label is complementary to a dendrite and includes a 12 base pair overhang. The eraser is fully complementary to the label, including the 12 base pair overhang. To initiate a label replacement, an eraser oligonucleotide is added to a previously labeled sample. The hybridization of the eraser to the overhang of the label will trigger a branch-migration event such that an eraser-label dsDNA oligonucleotide dimer will be generated as the label detached from the dendrite. The eraser-label dimer can then be washed away. Finally, a new label is added to the sample. These label-erase-label cycles can be repeated n times to generate barcodes. In comparison to the label-quench-label approach, this method is simpler and cheaper.

Label-Quench-Label Protocol
Assuming the Sample is in 5×SSCT
1. Add 2 µl of 1 µM label1 per 100 µl
2. Hybridize for 2 hours at RT°
3. Wash 3×10 minutes in 5×SSCT
4. Image
5. Add 2 µl of 1 µM label2 per 100 µl
6. Hybridize for 2 hours at RT°
7. Wash 3×10 minutes in 5×SSCT
8. Image Label-Erase-Label Protocol
Assuming the Sample is in 5×SSCT
1. Add 2 µl of 1 µM label1 per 100 µl
2. Hybridize for 2 hours at RT°
3. Wash 3×10 minutes in 5×SSCT
4. Image
5. Add 2 µl of 1 µM label2 and eraser per 100 µl.
6. Hybridize for 2 hours at RT°
7. Wash 3×10 minutes in 5×SSCT
8. Image The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are fallopian tube epithelium, cells, organoids, and tissue products thereof, methods of generating fallopian tube epithelium, prognostic and/or diagnostic panels that include nucleic acid, peptide and proteins sequences associated with cancers such as ovarian cancer, and the techniques associated with the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. An assembly, comprising:
  at least two molecules, wherein each molecule comprises:
    a) a nucleic acid hairpin loop,
    b) a nucleic acid stem,
    c) nucleic acid dendrites comprising a binding dendrite and an extension dendrite, and
    d) an organic polymer comprising polyethylene glycol, and further wherein the nucleic acid hairpin loop sequence of at least one first molecule is complementary to the nucleic acid binding dendrite sequence of at least one second molecule, and wherein the nucleic acid hairpin loop sequence of the at least one second molecule is complementary to the nucleic acid binding dendrite sequence of the at least one first molecule; and
  at least one nucleic acid trigger coupled to an analyte binding agent, wherein the nucleic acid trigger is complementary to the nucleic acid stem and the binding dendrite of one of the at least two molecules.

2. The assembly of claim 1, wherein the hairpin loop sequence and the binding dendrite sequence are each about 6-10 nucleotides.

3. The assembly of claim 1, wherein the hairpin loop sequence and the binding dendrite sequence are each about 11-13 nucleotides.

4. The assembly of claim 1, wherein the extension dendrite comprises about 13-16 nucleotides.

5. The assembly of claim 1, wherein the extension dendrite comprises about 10-25 nucleotides.

6. The assembly of claim 1, wherein the nucleic acid trigger comprises about 12-48 nucleotides.

7. The assembly of claim 1, wherein the nucleic acid trigger comprises about 34-38 nucleotides.

8. The assembly of claim 1, wherein the nucleic acid stem comprises about 6-15 nucleotides.

9. The assembly of claim 1, wherein the nucleic acid stem comprises about 22-26 nucleotides.

10. The assembly of claim 1, wherein polyethylene glycol comprises about 16-20 carbon lengths.

11. The assembly of claim 1, wherein the analyte binding agent comprises a polynucleotide.

12. The assembly of claim 1, wherein the analyte binding agent comprises a peptide or protein.

13. The assembly of claim 1, wherein the analyte binding agent comprises an antibody.

14. The assembly of claim 1, further comprising a labeling polynucleotide complementary to the extension dendrite of one of the at least two molecules.

15. The assembly of claim 14, wherein the labeling polynucleotide further comprises fluorophores, chromophores, chromogens, quantum dots, fluorescent microspheres, nanoparticles, elemental labels, metal chelating polymers, barcodes and/or sequential barcodes.

16. The assembly of claim 1, wherein the assembly further comprises at least two additional molecules, wherein each of the at least two additional molecules comprises:
  a) a nucleic acid hairpin loop,
  b) a nucleic acid stem,
  c) nucleic acid dendrites comprising a binding dendrite and an extension dendrite, and
  d) an organic polymer comprising polyethylene glycol, and further wherein the nucleic acid hairpin loop sequence of a first one of the at least two additional molecules is complementary to the nucleic acid binding dendrite sequence of a second one of the at least two additional molecules, and also wherein the nucleic acid hairpin loop sequence of the second one of the at least two additional molecules is complementary to the nucleic acid binding dendrite sequence of the first one of the at least two additional molecules; and
  a linker comprising a nucleic acid address complementary to an extension dendrite of the at least two molecule, and
  a second nucleic acid trigger complementary to a nucleic acid stem and a binding dendrite of the at least two additional molecules.

17. The assembly of claim 16, further comprising a labeling polynucleotide complementary to an extension dendrite of the at least two additional molecules.

18. The assembly of claim 17, wherein the labeling polynucleotide further comprises fluorophores, chromophores, chromogens, quantum dots, fluorescent microspheres, nanoparticles, elemental labels, metal chelating polymers, barcodes and/or sequential barcodes.

19. A method of polymerization to form an assembly, comprising:
  adding at least two molecules, each comprising:
    a nucleic acid hairpin loop,
    a nucleic acid stem,
    nucleic acid dendrites comprising a binding dendrite and an extension dendrite, and
    an organic polymer comprising polyethylene glycol,
    wherein the nucleic acid hairpin loop sequence of at least one first molecule is complementary to the nucleic acid binding dendrite sequence of at least one second molecule, and wherein the nucleic acid hairpin loop sequence of the at least one second molecule is complementary to the nucleic acid binding dendrite sequence of the at least one first molecule;
  further adding a trigger molecule comprising a nucleic acid, wherein the trigger molecule is coupled to an analyte binding agent, and wherein the nucleic acid of the trigger molecule is complementary to the nucleic acid stem and the binding dendrite of one of the at least two molecules; and triggering self-assembled polymerization of the at least two molecules, thereby forming the assembly.

20. The method of claim 19, comprising generating a detectable signal by binding a labeling polynucleotide complementary to the extension dendrite of one of the at least two molecules, wherein the labeling polynucleotide comprises a labeling agent.

21. The method of claim 19, further comprising adding: at least two additional molecules, wherein each of the at least two additional molecules comprises:
  a) a nucleic acid hairpin loop,
  b) a nucleic acid stem,
  c) nucleic acid dendrites comprising a binding dendrite and an extension dendrite, and
  d) an organic polymer comprising polyethylene glycol, and further wherein the nucleic acid hairpin loop sequence of a first one of the at least two additional molecules is complementary to the nucleic acid binding dendrite sequence of a second one of the at least two additional molecules, and also wherein the nucleic acid hairpin loop sequence of the second one of the at least two additional molecules is complementary to the nucleic acid binding dendrite sequence of the first one of the at least two additional molecules; and a linker comprising a nucleic acid address complementary to an extension dendrite of the at least two molecule, and a second nucleic acid trigger complementary to a nucleic acid stem and a binding dendrite of the at least two additional molecules.

* * * * *

SEQUENCE LISTING

<160> NUMBER OF SEQ ID NOS: 84

<210> SEQ ID NO 1
<211> LENGTH: 36
<212> TYPE: DNA
<213> ORGANISM: Artificial Sequence
<220> FEATURE:
<223> OTHER INFORMATION: TRIGGER 1

<400> SEQUENCE: 1
gtcccactct cacctcaccc gcaccatttc atttcc                                36

<210> SEQ ID NO 2
<211> LENGTH: 36
<212> TYPE: DNA
<213> ORGANISM: Artificial Sequence
<220> FEATURE:
<223> OTHER INFORMATION: TRIGGER 2

<400> SEQUENCE: 2
ccttatctat tcgtcccact ctcacctcac ccgcac                                36

<210> SEQ ID NO 3
<211> LENGTH: 72
<212> TYPE: DNA
<213> ORGANISM: Artificial Sequence
<220> FEATURE:
<223> OTHER INFORMATION: MONOMER 1A

<400> SEQUENCE: 3
ggaaatgaaa tggtgcgggt gaggtgagag tgggacccct atctattcgt cccactctca      60
cctcacccgc ac                                                          72

<210> SEQ ID NO 4
<211> LENGTH: 15
<212> TYPE: DNA
<213> ORGANISM: Artificial Sequence
<220> FEATURE:
<223> OTHER INFORMATION: MONOMER 1B

<400> SEQUENCE: 4
actaacccta aacac                                                       15

<210> SEQ ID NO 5
<211> LENGTH: 15
<212> TYPE: DNA
<213> ORGANISM: Artificial Sequence
<220> FEATURE:
<223> OTHER INFORMATION: MONOMER 2A

<400> SEQUENCE: 5
ctccactcat acacc                                                       15

<210> SEQ ID NO 6
<211> LENGTH: 72
<212> TYPE: DNA
<213> ORGANISM: Artificial Sequence
<220> FEATURE:
<223> OTHER INFORMATION: MONOMER 2B

<400> SEQUENCE: 6
gtcccactct cacctcaccc gcaccatttc atttccgtgc gggtgaggtg agagtgggac      60
gaatagataa gg                                                          72

<210> SEQ ID NO 7
<211> LENGTH: 36
<212> TYPE: DNA
<213> ORGANISM: Artificial Sequence
<220> FEATURE:
<223> OTHER INFORMATION: TRIGGER 1

<400> SEQUENCE: 7
caccgtccca tccatcccag cctccaatac aatacc    36

<210> SEQ ID NO 8
<211> LENGTH: 36
<212> TYPE: DNA
<213> ORGANISM: Artificial Sequence
<220> FEATURE:
<223> OTHER INFORMATION: TRIGGER 2

<400> SEQUENCE: 8
cctaatcaaa tccaccgtcc catccatccc agcctc    36

<210> SEQ ID NO 9
<211> LENGTH: 72
<212> TYPE: DNA
<213> ORGANISM: Artificial Sequence
<220> FEATURE:
<223> OTHER INFORMATION: MONOMER 1A

<400> SEQUENCE: 9
ggtattgtat tggaggctgg gatggatggg acggtgccta atcaaatcca ccgtcccatc    60
catcccagcc tc    72

<210> SEQ ID NO 10
<211> LENGTH: 15
<212> TYPE: DNA
<213> ORGANISM: Artificial Sequence
<220> FEATURE:
<223> OTHER INFORMATION: MONOMER 1B

<400> SEQUENCE: 10
atctcatctc atccc    15

<210> SEQ ID NO 11
<211> LENGTH: 15
<212> TYPE: DNA
<213> ORGANISM: Artificial Sequence
<220> FEATURE:
<223> OTHER INFORMATION: MONOMER 2A

<400> SEQUENCE: 11
ttccacttac tcccg    15

<210> SEQ ID NO 12
<211> LENGTH: 72
<212> TYPE: DNA
<213> ORGANISM: Artificial Sequence
<220> FEATURE:
<223> OTHER INFORMATION: MONOMER 2B

<400> SEQUENCE: 12
caccgtccca tccatcccag cctccaatac aataccgagg ctgggatgga tgggacggtg    60
gatttgatta gg    72

<210> SEQ ID NO 13
<211> LENGTH: 36
<212> TYPE: DNA
<213> ORGANISM: Artificial Sequence
<220> FEATURE:
<223> OTHER INFORMATION: TRIGGER 1

<400> SEQUENCE: 13
ctgcctcacc tactccctc gctccaaatc aaatcc    36

```
<210> SEQ ID NO 14
<211> LENGTH: 36
<212> TYPE: DNA
<213> ORGANISM: Artificial Sequence
<220> FEATURE:
<223> OTHER INFORMATION: TRIGGER 2

<400> SEQUENCE: 14
cctaaactaa tcctgcctca cctactaccc tcgctc                                  36

<210> SEQ ID NO 15
<211> LENGTH: 72
<212> TYPE: DNA
<213> ORGANISM: Artificial Sequence
<220> FEATURE:
<223> OTHER INFORMATION: MONOMER 1A

<400> SEQUENCE: 15
ggatttgatt tggagcgagg gtagtaggtg aggcagccta aactaatcct gcctcaccta        60
ctaccctcgc tc                                                            72

<210> SEQ ID NO 16
<211> LENGTH: 15
<212> TYPE: DNA
<213> ORGANISM: Artificial Sequence
<220> FEATURE:
<223> OTHER INFORMATION: MONOMER 1B

<400> SEQUENCE: 16
acccttacct ctacc                                                         15

<210> SEQ ID NO 17
<211> LENGTH: 15
<212> TYPE: DNA
<213> ORGANISM: Artificial Sequence
<220> FEATURE:
<223> OTHER INFORMATION: MONOMER 2A

<400> SEQUENCE: 17
ctccatccat ctcac                                                         15

<210> SEQ ID NO 18
<211> LENGTH: 72
<212> TYPE: DNA
<213> ORGANISM: Artificial Sequence
<220> FEATURE:
<223> OTHER INFORMATION: MONOMER 2B

<400> SEQUENCE: 18
ctgcctcacc tactaccctc gctccaaatc aaatccgagc gagggtagta ggtgaggcag        60
gattagttta gg                                                            72

<210> SEQ ID NO 19
<211> LENGTH: 36
<212> TYPE: DNA
<213> ORGANISM: Artificial Sequence
<220> FEATURE:
<223> OTHER INFORMATION: TRIGGER 1

<400> SEQUENCE: 19
ctcgccctta cacctcaccc gctcctaaac taaacc                                  36

<210> SEQ ID NO 20
<211> LENGTH: 36
<212> TYPE: DNA
```

```
<213> ORGANISM: Artificial Sequence
<220> FEATURE:
<223> OTHER INFORMATION: TRIGGER 2

<400> SEQUENCE: 20
cctttacttt acctcgccct tacacctcac ccgctc                                 36

<210> SEQ ID NO 21
<211> LENGTH: 72
<212> TYPE: DNA
<213> ORGANISM: Artificial Sequence
<220> FEATURE:
<223> OTHER INFORMATION: MONOMER 1A

<400> SEQUENCE: 21
ggtttagttt aggagcgggt gaggtgtaag ggcgagcctt tactttacct cgcccttaca       60
cctcacccgc tc                                                           72

<210> SEQ ID NO 22
<211> LENGTH: 15
<212> TYPE: DNA
<213> ORGANISM: Artificial Sequence
<220> FEATURE:
<223> OTHER INFORMATION: MONOMER 1B

<400> SEQUENCE: 22
attcccatac tcttc                                                        15

<210> SEQ ID NO 23
<211> LENGTH: 15
<212> TYPE: DNA
<213> ORGANISM: Artificial Sequence
<220> FEATURE:
<223> OTHER INFORMATION: MONOMER 2A

<400> SEQUENCE: 23
cttccaatca tcccg                                                        15

<210> SEQ ID NO 24
<211> LENGTH: 72
<212> TYPE: DNA
<213> ORGANISM: Artificial Sequence
<220> FEATURE:
<223> OTHER INFORMATION: MONOMER 2B

<400> SEQUENCE: 24
ctcgccctta cacctcaccc gctcctaaac taaaccgagc gggtgaggtg taagggcgag       60
gtaaagtaaa gg                                                           72

<210> SEQ ID NO 25
<211> LENGTH: 36
<212> TYPE: DNA
<213> ORGANISM: Artificial Sequence
<220> FEATURE:
<223> OTHER INFORMATION: TRIGGER 1

<400> SEQUENCE: 25
ctgcctcacc tccaactccc gctcctattc atttcc                                 36

<210> SEQ ID NO 26
<211> LENGTH: 36
<212> TYPE: DNA
<213> ORGANISM: Artificial Sequence
<220> FEATURE:
<223> OTHER INFORMATION: TRIGGER 2
```

```
<400> SEQUENCE: 26
cctttactat tcctgcctca cctccaactc ccgctc                                36

<210> SEQ ID NO 27
<211> LENGTH: 72
<212> TYPE: DNA
<213> ORGANISM: Artificial Sequence
<220> FEATURE:
<223> OTHER INFORMATION: MONOMER 1A

<400> SEQUENCE: 27
ggaaatgaat aggagcggga gttggaggtg aggcagcctt tactattcct gcctcacctc     60
caactcccgc tc                                                         72

<210> SEQ ID NO 28
<211> LENGTH: 15
<212> TYPE: DNA
<213> ORGANISM: Artificial Sequence
<220> FEATURE:
<223> OTHER INFORMATION: MONOMER 1B

<400> SEQUENCE: 28
acactctaca actac                                                      15

<210> SEQ ID NO 29
<211> LENGTH: 15
<212> TYPE: DNA
<213> ORGANISM: Artificial Sequence
<220> FEATURE:
<223> OTHER INFORMATION: MONOMER 2A

<400> SEQUENCE: 29
ccaatcaatc cctac                                                      15

<210> SEQ ID NO 30
<211> LENGTH: 72
<212> TYPE: DNA
<213> ORGANISM: Artificial Sequence
<220> FEATURE:
<223> OTHER INFORMATION: MONOMER 2B

<400> SEQUENCE: 30
ctgcctcacc tccaactccc gctcctattc atttccgagc gggagttgga ggtgaggcag     60
gaatagtaaa gg                                                         72

<210> SEQ ID NO 31
<211> LENGTH: 36
<212> TYPE: DNA
<213> ORGANISM: Artificial Sequence
<220> FEATURE:
<223> OTHER INFORMATION: TRIGGER 1

<400> SEQUENCE: 31
caccgaccat ccatacaccg ccacctttac atttcc                               36

<210> SEQ ID NO 32
<211> LENGTH: 36
<212> TYPE: DNA
<213> ORGANISM: Artificial Sequence
<220> FEATURE:
<223> OTHER INFORMATION: TRIGGER 2

<400> SEQUENCE: 32
```
cctttactat tccaccgacc atccatacac cgccac                                    36

<210> SEQ ID NO 33
<211> LENGTH: 72
<212> TYPE: DNA
<213> ORGANISM: Artificial Sequence
<220> FEATURE:
<223> OTHER INFORMATION: MONOMER 1A

<400> SEQUENCE: 33
ggaaatgtaa aggtggcggt gtatggatgg tcggtgcctt tactattcca ccgaccatcc    60
atacaccgcc ac                                                        72

<210> SEQ ID NO 34
<211> LENGTH: 15
<212> TYPE: DNA
<213> ORGANISM: Artificial Sequence
<220> FEATURE:
<223> OTHER INFORMATION: MONOMER 1B

<400> SEQUENCE: 34
tcactaacta aactc                                                     15

<210> SEQ ID NO 35
<211> LENGTH: 15
<212> TYPE: DNA
<213> ORGANISM: Artificial Sequence
<220> FEATURE:
<223> OTHER INFORMATION: MONOMER 2A

<400> SEQUENCE: 35
ttcaatcatc accag                                                     15

<210> SEQ ID NO 36
<211> LENGTH: 72
<212> TYPE: DNA
<213> ORGANISM: Artificial Sequence
<220> FEATURE:
<223> OTHER INFORMATION: MONOMER 2B

<400> SEQUENCE: 36
caccgaccat ccatacaccg ccacctttac atttccgtgg cggtgtatgg atggtcggtg    60
gaatagtaaa gg                                                        72

<210> SEQ ID NO 37
<211> LENGTH: 36
<212> TYPE: DNA
<213> ORGANISM: Artificial Sequence
<220> FEATURE:
<223> OTHER INFORMATION: TRIGGER 1

<400> SEQUENCE: 37
cagcctcacc ataacatcac cgacctaaac taaacc                              36

<210> SEQ ID NO 38
<211> LENGTH: 36
<212> TYPE: DNA
<213> ORGANISM: Artificial Sequence
<220> FEATURE:
<223> OTHER INFORMATION: TRIGGER 2

<400> SEQUENCE: 38
cctttacatt tccagcctca ccataacatc accgac                              36

```
<210> SEQ ID NO 39
<211> LENGTH: 72
<212> TYPE: DNA
<213> ORGANISM: Artificial Sequence
<220> FEATURE:
<223> OTHER INFORMATION: MONOMER 1A

<400> SEQUENCE: 39
ggtttagttt aggtcggtga tgttatggtg aggctgcctt tacatttcca gcctcaccat      60
aacatcaccg ac                                                         72

<210> SEQ ID NO 40
<211> LENGTH: 15
<212> TYPE: DNA
<213> ORGANISM: Artificial Sequence
<220> FEATURE:
<223> OTHER INFORMATION: MONOMER 1B

<400> SEQUENCE: 40
aatccaatca catcc                                                      15

<210> SEQ ID NO 41
<211> LENGTH: 15
<212> TYPE: DNA
<213> ORGANISM: Artificial Sequence
<220> FEATURE:
<223> OTHER INFORMATION: MONOMER 2A

<400> SEQUENCE: 41
cttcaatctc acccg                                                      15

<210> SEQ ID NO 42
<211> LENGTH: 72
<212> TYPE: DNA
<213> ORGANISM: Artificial Sequence
<220> FEATURE:
<223> OTHER INFORMATION: MONOMER 2B

<400> SEQUENCE: 42
cagcctcacc ataacatcac cgacctaaac taaaccgtcg gtgatgttat ggtgaggctg      60
gaaatgtaaa gg                                                         72

<210> SEQ ID NO 43
<211> LENGTH: 36
<212> TYPE: DNA
<213> ORGANISM: Artificial Sequence
<220> FEATURE:
<223> OTHER INFORMATION: TRIGGER 1

<400> SEQUENCE: 43
ctccgacctc tactaccctg cctccataac aattcc                               36

<210> SEQ ID NO 44
<211> LENGTH: 36
<212> TYPE: DNA
<213> ORGANISM: Artificial Sequence
<220> FEATURE:
<223> OTHER INFORMATION: TRIGGER 2

<400> SEQUENCE: 44
ccaaatctaa acctccgacc tctactaccc tgcctc                               36

<210> SEQ ID NO 45
<211> LENGTH: 72
<212> TYPE: DNA
```

```
<213> ORGANISM: Artificial Sequence
<220> FEATURE:
<223> OTHER INFORMATION: MONOMER 1A

<400> SEQUENCE: 45
ggaattgtta tggaggcagg gtagtagagg tcggagccaa atctaaacct ccgacctcta      60
ctaccctgcc tc                                                          72

<210> SEQ ID NO 46
<211> LENGTH: 15
<212> TYPE: DNA
<213> ORGANISM: Artificial Sequence
<220> FEATURE:
<223> OTHER INFORMATION: MONOMER 1B

<400> SEQUENCE: 46
accctactct cactc                                                       15

<210> SEQ ID NO 47
<211> LENGTH: 15
<212> TYPE: DNA
<213> ORGANISM: Artificial Sequence
<220> FEATURE:
<223> OTHER INFORMATION: MONOMER 2A

<400> SEQUENCE: 47
tcacttatac tcctg                                                       15

<210> SEQ ID NO 48
<211> LENGTH: 72
<212> TYPE: DNA
<213> ORGANISM: Artificial Sequence
<220> FEATURE:
<223> OTHER INFORMATION: MONOMER 2B

<400> SEQUENCE: 48
ctccgacctc tactccctg cctccataac aattccgagg cagggtagta gaggtcggag       60
gtttagattt gg                                                          72

<210> SEQ ID NO 49
<211> LENGTH: 36
<212> TYPE: DNA
<213> ORGANISM: Artificial Sequence
<220> FEATURE:
<223> OTHER INFORMATION: TRIGGER 1

<400> SEQUENCE: 49
cagccacttt caccatacac cgacctttac tttacc                                36

<210> SEQ ID NO 50
<211> LENGTH: 36
<212> TYPE: DNA
<213> ORGANISM: Artificial Sequence
<220> FEATURE:
<223> OTHER INFORMATION: TRIGGER 2

<400> SEQUENCE: 50
ccaaatcaat accagccact ttcaccatac accgac                                36

<210> SEQ ID NO 51
<211> LENGTH: 72
<212> TYPE: DNA
<213> ORGANISM: Artificial Sequence
<220> FEATURE:
<223> OTHER INFORMATION: MONOMER 1A
```

<400> SEQUENCE: 51
ggtaaagtaa aggtcggtgt atggtgaaag tggctgccaa atcaatacca gccactttca    60
ccatacaccg ac                                                        72

<210> SEQ ID NO 52
<211> LENGTH: 15
<212> TYPE: DNA
<213> ORGANISM: Artificial Sequence
<220> FEATURE:
<223> OTHER INFORMATION: MONOMER 1B

<400> SEQUENCE: 52
aatcccaatc caaac                                                     15

<210> SEQ ID NO 53
<211> LENGTH: 15
<212> TYPE: DNA
<213> ORGANISM: Artificial Sequence
<220> FEATURE:
<223> OTHER INFORMATION: MONOMER 2A

<400> SEQUENCE: 53
ctttcatact actcc                                                     15

<210> SEQ ID NO 54
<211> LENGTH: 72
<212> TYPE: DNA
<213> ORGANISM: Artificial Sequence
<220> FEATURE:
<223> OTHER INFORMATION: MONOMER 2B

<400> SEQUENCE: 54
cagccacttt caccatacac cgacctttac tttaccgtcg gtgtatggtg aaagtggctg    60
gtattgattt gg                                                        72

<210> SEQ ID NO 55
<211> LENGTH: 36
<212> TYPE: DNA
<213> ORGANISM: Artificial Sequence
<220> FEATURE:
<223> OTHER INFORMATION: TRIGGER 1

<400> SEQUENCE: 55
ctcgcccact cacctcaccc gcaccttatc atttcc                              36

<210> SEQ ID NO 56
<211> LENGTH: 36
<212> TYPE: DNA
<213> ORGANISM: Artificial Sequence
<220> FEATURE:
<223> OTHER INFORMATION: TRIGGER 2

<400> SEQUENCE: 56
ccaaatcaaa tcctcgccca ctcacctcac ccgcac                              36

<210> SEQ ID NO 57
<211> LENGTH: 72
<212> TYPE: DNA
<213> ORGANISM: Artificial Sequence
<220> FEATURE:
<223> OTHER INFORMATION: MONOMER 1A

<400> SEQUENCE: 57

```
ggaaatgata aggtgcgggt gaggtgagtg ggcgagccaa atcaaatcct cgcccactca    60
cctcacccgc ac                                                        72

<210> SEQ ID NO 58
<211> LENGTH: 15
<212> TYPE: DNA
<213> ORGANISM: Artificial Sequence
<220> FEATURE:
<223> OTHER INFORMATION: MONOMER 1B

<400> SEQUENCE: 58
taccctaacc tctac                                                     15

<210> SEQ ID NO 59
<211> LENGTH: 15
<212> TYPE: DNA
<213> ORGANISM: Artificial Sequence
<220> FEATURE:
<223> OTHER INFORMATION: MONOMER 2A

<400> SEQUENCE: 59
cctttactac tcccg                                                     15

<210> SEQ ID NO 60
<211> LENGTH: 72
<212> TYPE: DNA
<213> ORGANISM: Artificial Sequence
<220> FEATURE:
<223> OTHER INFORMATION: MONOMER 2B

<400> SEQUENCE: 60
ctcgcccact cacctcaccc gcaccttatc atttccgtgc gggtgaggtg agtgggcgag    60
gatttgattt gg                                                        72

<210> SEQ ID NO 61
<211> LENGTH: 25
<212> TYPE: DNA
<213> ORGANISM: Artificial Sequence
<220> FEATURE:
<223> OTHER INFORMATION: TRIGGER 1

<400> SEQUENCE: 61
cacgctccac tccacctaac taacc                                          25

<210> SEQ ID NO 62
<211> LENGTH: 25
<212> TYPE: DNA
<213> ORGANISM: Artificial Sequence
<220> FEATURE:
<223> OTHER INFORMATION: TRIGGER 2

<400> SEQUENCE: 62
ccatacatac cacgctccac tccac                                          25

<210> SEQ ID NO 63
<211> LENGTH: 50
<212> TYPE: DNA
<213> ORGANISM: Artificial Sequence
<220> FEATURE:
<223> OTHER INFORMATION: MONOMER 1A

<400> SEQUENCE: 63
ggttagttag gtggagtgga gcgtgccata cataccacgc tccactccac               50
```

```
<210> SEQ ID NO 64
<211> LENGTH: 12
<212> TYPE: DNA
<213> ORGANISM: Artificial Sequence
<220> FEATURE:
<223> OTHER INFORMATION: MONOMER 1B

<400> SEQUENCE: 64
atcatctcat cc                                                         12

<210> SEQ ID NO 65
<211> LENGTH: 12
<212> TYPE: DNA
<213> ORGANISM: Artificial Sequence
<220> FEATURE:
<223> OTHER INFORMATION: MONOMER 2A

<400> SEQUENCE: 65
cctaaatctc ta                                                         12

<210> SEQ ID NO 66
<211> LENGTH: 48
<212> TYPE: DNA
<213> ORGANISM: Artificial Sequence
<220> FEATURE:
<223> OTHER INFORMATION: MONOMER 2B

<400> SEQUENCE: 66
cacgctccac tccacctaac taaccgtgga gtggagcgtg gtatgtat                  48

<210> SEQ ID NO 67
<211> LENGTH: 18
<212> TYPE: DNA
<213> ORGANISM: Artificial Sequence
<220> FEATURE:
<223> OTHER INFORMATION: TRIGGER 1

<400> SEQUENCE: 67
atcgcctagc cttaatcc                                                   18

<210> SEQ ID NO 68
<211> LENGTH: 18
<212> TYPE: DNA
<213> ORGANISM: Artificial Sequence
<220> FEATURE:
<223> OTHER INFORMATION: TRIGGER 2

<400> SEQUENCE: 68
cctttatcat cgcctagc                                                   18

<210> SEQ ID NO 69
<211> LENGTH: 18
<212> TYPE: DNA
<213> ORGANISM: Artificial Sequence
<220> FEATURE:
<223> OTHER INFORMATION: MONOMER 1A

<400> SEQUENCE: 69
aacgccaacc caaatacc                                                   18

<210> SEQ ID NO 70
<211> LENGTH: 36
<212> TYPE: DNA
<213> ORGANISM: Artificial Sequence
<220> FEATURE:
<223> OTHER INFORMATION: MONOMER 1B
```

```
<400> SEQUENCE: 70
atcgcctagc cttaatccgc taggcgatga taaagg                               36

<210> SEQ ID NO 71
<211> LENGTH: 36
<212> TYPE: DNA
<213> ORGANISM: Artificial Sequence
<220> FEATURE:
<223> OTHER INFORMATION: MONOMER 2A

<400> SEQUENCE: 71
ggattaaggc taggcgatcc tttatcatcg cctagc                               36

<210> SEQ ID NO 72
<211> LENGTH: 18
<212> TYPE: DNA
<213> ORGANISM: Artificial Sequence
<220> FEATURE:
<223> OTHER INFORMATION: MONOMER 2B

<400> SEQUENCE: 72
cctatttcaa cgccaacc                                                   18

<210> SEQ ID NO 73
<211> LENGTH: 16
<212> TYPE: DNA
<213> ORGANISM: Artificial Sequence
<220> FEATURE:
<223> OTHER INFORMATION: TRIGGER 1

<400> SEQUENCE: 73
aacccgaacc taaagc                                                     16

<210> SEQ ID NO 74
<211> LENGTH: 16
<212> TYPE: DNA
<213> ORGANISM: Artificial Sequence
<220> FEATURE:
<223> OTHER INFORMATION: TRIGGER 2

<400> SEQUENCE: 74
gctttaaacc cgaacc                                                     16

<210> SEQ ID NO 75
<211> LENGTH: 16
<212> TYPE: DNA
<213> ORGANISM: Artificial Sequence
<220> FEATURE:
<223> OTHER INFORMATION: MONOMER 1A

<400> SEQUENCE: 75
gctttaggtt cgggtt                                                     16

<210> SEQ ID NO 76
<211> LENGTH: 32
<212> TYPE: DNA
<213> ORGANISM: Artificial Sequence
<220> FEATURE:
<223> OTHER INFORMATION: MONOMER 1B

<400> SEQUENCE: 76
gctttaaacc cgaaccatac ccacaccaac cc                                   32

<210> SEQ ID NO 77
<211> LENGTH: 32
```

```
<212> TYPE: DNA
<213> ORGANISM: Artificial Sequence
<220> FEATURE:
<223> OTHER INFORMATION: MONOMER 2A

<400> SEQUENCE: 77
cccaaccacc accaataacc cgaacctaaa gc                                    32

<210> SEQ ID NO 78
<211> LENGTH: 16
<212> TYPE: DNA
<213> ORGANISM: Artificial Sequence
<220> FEATURE:
<223> OTHER INFORMATION: MONOMER 2B

<400> SEQUENCE: 78
ggttcgggtt taaagc                                                      16

<210> SEQ ID NO 79
<211> LENGTH: 14
<212> TYPE: DNA
<213> ORGANISM: Artificial Sequence
<220> FEATURE:
<223> OTHER INFORMATION: TRIGGER 1

<400> SEQUENCE: 79 cgccaccta aacc                                                         14

<210> SEQ ID NO 80
<211> LENGTH: 14
<212> TYPE: DNA
<213> ORGANISM: Artificial Sequence
<220> FEATURE:
<223> OTHER INFORMATION: TRIGGER 2

<400> SEQUENCE: 80
ccatttcgcc accc                                                        14

<210> SEQ ID NO 81
<211> LENGTH: 10
<212> TYPE: DNA
<213> ORGANISM: Artificial Sequence
<220> FEATURE:
<223> OTHER INFORMATION: MONOMER 1A

<400> SEQUENCE: 81
ggtttagggt                                                             10

<210> SEQ ID NO 82
<211> LENGTH: 28
<212> TYPE: DNA
<213> ORGANISM: Artificial Sequence
<220> FEATURE:
<223> OTHER INFORMATION: MONOMER 1B

<400> SEQUENCE: 82
ggcgccattt cgccacccat ctcttccc                                         28

<210> SEQ ID NO 83
<211> LENGTH: 28
<212> TYPE: DNA
<213> ORGANISM: Artificial Sequence
<220> FEATURE:
<223> OTHER INFORMATION: MONOMER 2A

<400> SEQUENCE: 83
```

```
ccctctacta cgccacccta aaccgggt                                        28

<210> SEQ ID NO 84
<211> LENGTH: 10
<212> TYPE: DNA
<213> ORGANISM: Artificial Sequence
<220> FEATURE:
<223> OTHER INFORMATION: MONOMER 2B

<400> SEQUENCE: 84
ggcgaaatgg                                                            10
```